United States Patent
Freudenberg et al.

(10) Patent No.: US 9,504,370 B2
(45) Date of Patent: Nov. 29, 2016

(54) MAGNETIC LOW PRODUCT INDICATOR

(71) Applicant: Ecolab USA Inc., St. Paul, MN (US)

(72) Inventors: Jared Ryan Freudenberg, Saint Louis Park, MN (US); Brian Joseph Doffing, Arden Hills, MN (US)

(73) Assignee: Ecolab USA Inc., St. Paul, MN (US)

( * ) Notice: Subject to any disclaimer, the term of this patent is extended or adjusted under 35 U.S.C. 154(b) by 182 days.

(21) Appl. No.: 14/280,787

(22) Filed: May 19, 2014

(65) Prior Publication Data

US 2014/0251006 A1  Sep. 11, 2014

Related U.S. Application Data

(63) Continuation-in-part of application No. 13/895,100, filed on May 15, 2013.

(60) Provisional application No. 61/734,532, filed on Dec. 7, 2012.

(51) Int. Cl.
  *G01F 23/20*  (2006.01)
  *A47L 11/40*  (2006.01)
  *A61L 2/18*  (2006.01)
  *B08B 3/04*  (2006.01)

(52) U.S. Cl.
  CPC ........ *A47L 11/4088* (2013.01); *A47L 11/4083* (2013.01); *A61L 2/18* (2013.01); *A61L 2202/15* (2013.01); *A61L 2202/17* (2013.01); *B08B 3/04* (2013.01)

(58) Field of Classification Search
  CPC ... H02N 15/00; H01F 7/0236; B05B 12/004; B67D 1/1247; A47L 11/4088; A47L 11/4083; A61L 2/18; A61L 2202/15; A61L 2202/17; B08B 3/04

USPC ............... 222/58, 64–67, 145, 77, 41–49; 73/54.18, 861.94, 290 R, 296, 314, 430, 73/865.3, DIG. 5; 335/285
  See application file for complete search history.

(56) References Cited

U.S. PATENT DOCUMENTS

| | | | |
|---|---|---|---|
| 3,687,209 A | 8/1972 | Goldberg | |
| 3,754,527 A * | 8/1973 | Jenkins | A01K 5/0291 119/51.11 |
| 3,768,696 A | 10/1973 | Laerdal | |
| 3,843,020 A * | 10/1974 | Bardeau | B67D 1/0085 137/408 |
| 3,992,941 A * | 11/1976 | McGoldrick | G01F 23/68 340/623 |
| 4,078,625 A | 3/1978 | Loeb | |

(Continued)

FOREIGN PATENT DOCUMENTS

| | | |
|---|---|---|
| GB | 1349945 A | 4/1974 |
| GB | 2452607 A | 3/2009 |
| JP | 6058519 A | 4/1985 |

*Primary Examiner* — Paul R Durand
*Assistant Examiner* — Charles P Cheyney
(74) *Attorney, Agent, or Firm* — Fredrikson & Byron, P.A.

(57) ABSTRACT

Embodiments include a dispenser for dispensing a product. The dispenser has a housing, a container, a container holder and a first holder magnetic element positioned on the container holder. The first holder magnetic element and a first stationary magnetic element interact to create a first magnetic force. The first magnetic force can induce the container holder to move. The position of the container holder along an axis of the container holder is correlated with the weight of the product remaining in the container. An indicator may alert user regarding the amount of product remaining in the container based on the position of the container holder.

26 Claims, 14 Drawing Sheets

(56) References Cited

U.S. PATENT DOCUMENTS

| | | | |
|---|---|---|---|
| 4,245,505 A | 1/1981 | Baynes | |
| 4,319,651 A | 3/1982 | Robichaud | |
| 4,491,023 A | 1/1985 | Graef | |
| 4,714,177 A * | 12/1987 | Morris | A01C 1/08 137/408 |
| 5,020,972 A * | 6/1991 | Nakayama | B67D 1/1243 141/83 |
| 5,190,189 A * | 3/1993 | Zimmer | B67D 1/0057 222/146.6 |
| 5,316,196 A * | 5/1994 | Reich | F04F 1/06 222/160 |
| 5,686,704 A | 11/1997 | Simser | |
| 5,782,382 A * | 7/1998 | Van Marcke | A47K 5/1214 222/105 |
| 5,864,097 A | 1/1999 | Alvino | |
| 6,246,017 B1 | 6/2001 | Yang | |
| 6,253,960 B1 * | 7/2001 | Bilskie | B67D 1/0057 222/129.2 |
| 6,284,987 B1 | 9/2001 | Al-Modiny | |
| 6,325,113 B1 | 12/2001 | Hathaway et al. | |
| 6,402,118 B1 * | 6/2002 | Nijsse | A47C 31/003 188/267 |
| 6,649,850 B2 | 11/2003 | Strohmeier | |
| 6,978,671 B1 | 12/2005 | Meggs et al. | |
| 7,211,908 B2 * | 5/2007 | Tamaki | F16C 29/00 310/12.25 |
| 9,245,679 B1 * | 1/2016 | Termain | H01F 7/06 |
| 2002/0124657 A1 * | 9/2002 | Wright | G01F 23/18 73/760 |
| 2004/0052029 A1 * | 3/2004 | Joachim | H02N 15/00 361/143 |
| 2005/0139003 A1 * | 6/2005 | Cochran | G01F 23/363 73/313 |
| 2009/0309440 A1 * | 12/2009 | Lieberman | H02N 15/00 310/90.5 |

* cited by examiner

MAGNETIC LOW PRODUCT INDICATOR

RELATED APPLICATION

This application is a continuation-in-part of application Ser. No. 13/895,100, filed on May 15, 2013, which claims priority to provisional application No. 61/734,532, filed on Dec. 7, 2012, the disclosure of each of which is hereby incorporated by reference in its entirety.

FIELD

This disclosure generally relates to dispensers that dispense a product from a container. Portions of this disclosure relate to systems and methods for indicating that the level of the product remaining in the container is low.

BACKGROUND

Dispensers that dispense a product from a container have many uses. Typically, such dispensers have an outlet that is fluidly connected to the container to draw the product out of the container. The product may be mixed with a liquid, such as a diluting solution (e.g., water) to form a mixture, either before or after reaching the outlet. Such dispensers are often used for dispensing a disinfectant, sanitizer (e.g., Quik-Care™ aerosol hand sanitizer, Ecolab Inc.) and the like for cleaning or disinfecting in a facility. Such facilities may include industrial, food and beverage packaging facilities (e.g., food/beverage packaging facilities and restaurants), healthcare facilities (e.g., hospitals), and other institutions and/or public areas (e.g., schools, office buildings etc.). Such dispensers may also be used in textile care industries (e.g., using laundry detergents), or in heavy industrial cleaning (e.g., machinery, industrial appliances). While quaternary ammonium compounds (sometimes referred to as "quat" disinfectant) have been typically used for disinfecting, such disinfectants require an exposure time of at least 10 minutes to interact with and destroy the cellular structure of microbial organisms. Other disinfectants such as peroxyacietic acid mixed with hydrogen peroxide forms a cleaning concentrate that can be diluted with water to form a mixture. Such a solution is typically more effective against most viruses and bacteria than quat disinfectants, which makes the peroxyacietic acid-hydrogen peroxide solution useful in many industrial (e.g., food packaging and beverage bottling plants) and healthcare facilities (e.g., hospitals).

Concentrated disinfectants such as peroxyacietic acid may typically be stored in rigid plastic containers of sufficient thickness to safely contain the product to prevent accidental spills, and avoid contact with an operator disinfecting a facility. Such containers can be opaque bottles to prevent exposing the disinfecting product to light or other types of radiation (e.g., ultraviolet radiation) which may cause deterioration of the disinfectant. U.S. Provisional Patent Application 61/734,532, filed Dec. 7, 2012, relates to a system for handling liquid products, the entire contents of which are hereby incorporated by reference, which describes a dispenser that may be used to dispense a cleaning solution using a product that undergoes degradation when exposed to ultraviolet (UV) radiation. Such degradable products stored in opaque containers that may prevent visual inspection of the level of the product remaining in the container. Alternatively, the container itself may be hidden from view when positioned within a housing or hidden from view by a protective cover of a dispensing equipment.

As the product is dispensed, the level of the product remaining within the container may drop, until the container is eventually empty or nearly empty. Many cleaning, sanitizing and/or disinfecting operations may need a predetermined quantity of the product in the container. A predetermined quantity may be required to effectively clean and/or disinfect a facility. For instance, a certain volume or concentration of disinfectant may be necessary at minimum, to remove microorganisms in a facility. If the dispenser were to have less than the required minimum of product, cleaning, sanitizing and/or disinfecting may not be satisfactory. Regulatory authorities may also determine the use of a predetermined quantity and/or concentration of the product for performing an operation. Additionally, an operator may want to know the level of the product within the container, and when the level reaches below a predetermined threshold, the operator can have adequate quantity of replacement product stocked in the inventory. Alerting the user with information about the product level may also ensure that the operator has sufficient amount of product for an operation, and any downtime due to insufficient quantity of product is avoided. In addition, compliance with regulations for safe handling and disposal may require that the container includes less than a predetermined quantity of product prior to flushing out the product and/or rinsing the container. It may be beneficial for the operator to stay informed of the level of the product even if the container is not empty.

SUMMARY OF THE INVENTION

Certain embodiments of the invention include a dispenser for dispensing a product. The dispenser may include a housing, a container positioned within the housing and a first holder magnetic element positioned on the container. The first holder magnetic element and the first stationary magnetic element interact to create a first magnetic force therebetween. The first magnetic force may be directed along a container axis. The first magnetic force can induce the container to move along the container axis in a first direction. The position of the container along the container axis is correlated with the weight of the product remaining in the container.

Certain embodiments of the invention include a container holder. The container holder may support the container. The first holder magnetic element can be positioned on the container holder. In such embodiments, the first magnetic force between the first holder magnetic element and the first stationary magnetic element can induce the container holder to move along a container holder axis in a first direction. The position of the container holder along the container holder axis is correlated with the weight of the product remaining in the container.

Some embodiments of the invention may include a second magnetic element positioned on the container holder. The second holder magnetic element can be adapted to create a second magnetic force due to interaction with a second stationary magnetic element positioned external to the housing. The second magnetic force may induce the container holder to move along the container holder axis in a second direction. The first and second directions may be parallel to a vertically upward direction. In some embodiments, the first magnetic force can be a repulsive force adapted to move the first magnetic element away from the first stationary magnetic element. In such embodiments, the second magnetic force can be an attractive force adapted to move the second magnetic element towards the second stationary magnetic element. In some embodiments, the first magnetic force is linearly proportional to the distance between the first magnetic element and the first stationary magnetic element. In alternate embodiments, the first magnetic force varies non-linearly with the distance between the first magnetic element and the first stationary magnetic element.

Certain embodiments of the invention include a dispenser provided with an indicator. The indicator can be configured for providing an indication to a user when a weight of the product in the container is below a first pre-determined weight of the product. The indicator can be correlated with the movement of the container holder induced by the first and/or second magnetic elements. The indicator may be configured such that it provides an indication when the container holder is at a first axial location (e.g., when the weight of the product is below a first predetermined weight). In some embodiments, the dispenser may include a sensor triggered by the movement of the container holder. The sensor can provide an indication of the weight of the product remaining in the container based on an axial position of the container holder along the container holder axis. The sensor can be, but is not limited to, one or more of a reed switch, a proximity sensor, a contact switch, an infrared switch, and an optical switch. Alternatively, the sensor can directly provide the weight of the product in the container. An exemplary sensor according to such embodiments may be a load cell, which may directly indicate if the weight of the product has reached predetermined minimum weight, and/or if the container is empty. Such weight-based sensors may not be correlated with the position/movement of the container, and may directly indicate the weight of product.

BRIEF DESCRIPTION OF THE DRAWINGS

The following drawings are illustrative of particular embodiments of the present invention and therefore do not limit the scope of the invention. The drawings are not necessarily to scale (unless so stated) and are intended for use in conjunction with the explanations in the following detailed description. Embodiments of the invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides some practical illustrations for implementing exemplary embodiments of the present invention. Examples of constructions, materials, dimensions, and manufacturing processes are provided for selected elements, and all other elements employ that which is known to those of ordinary skill in the field of the invention. Those skilled in the art will recognize that many of the noted examples have a variety of suitable alternatives.

Figure 1:
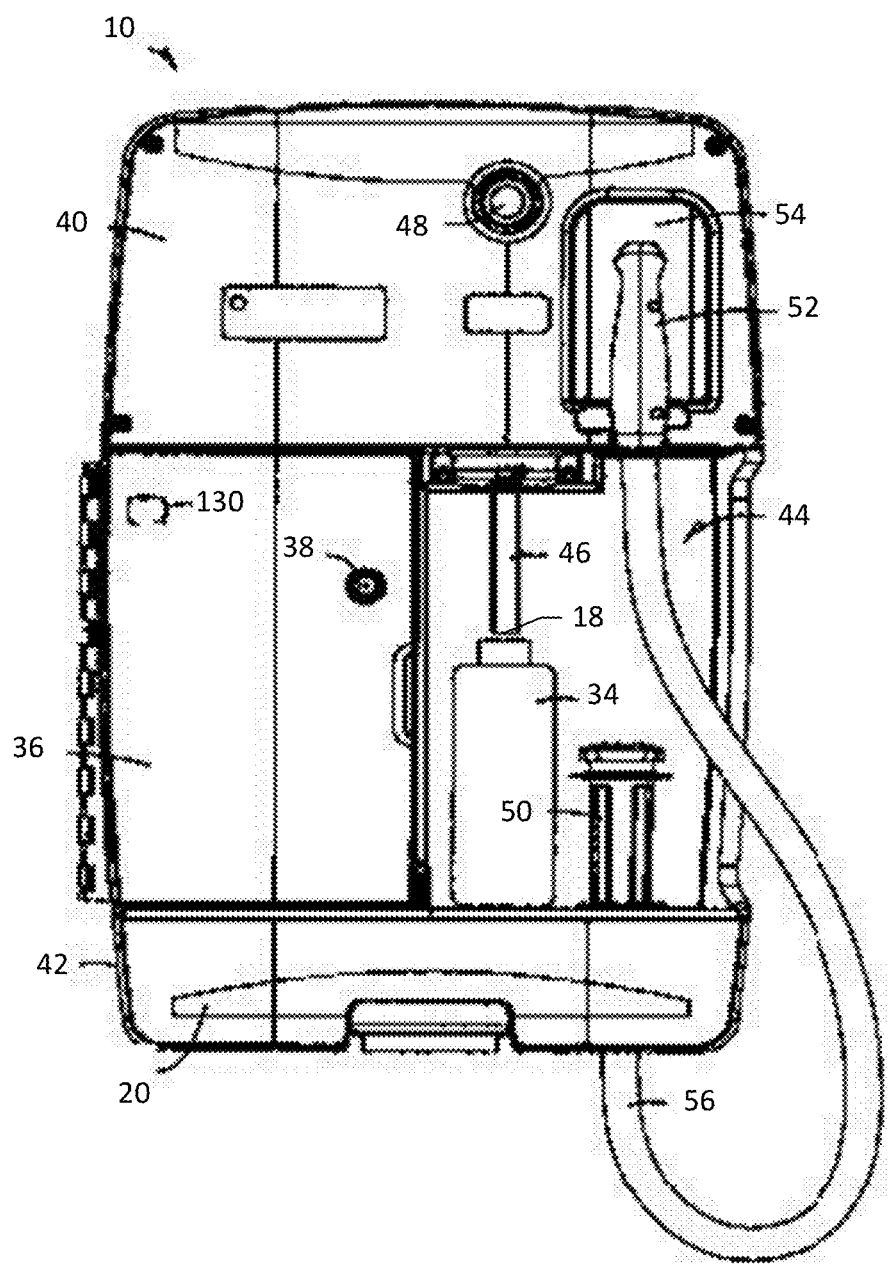
FIG. 1 is a front view of a dispenser according to some embodiments of the invention.
Figure 2:
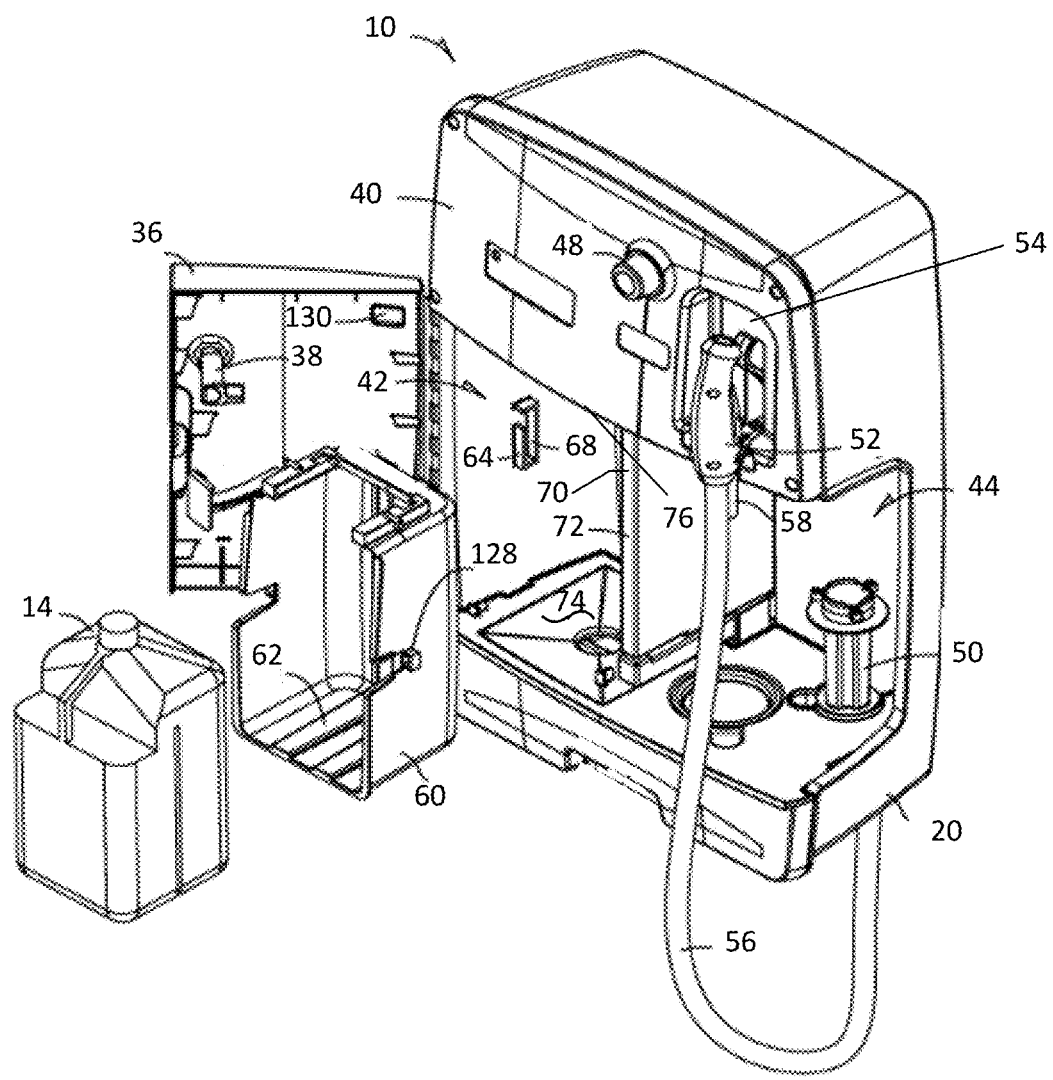
FIG. 2 is a perspective view of the dispenser of FIG. 1 with a door in an open position.

FIGS. 1 and 2 illustrate, respectively, a front elevation view and a front perspective view of a dispenser 10 according to one embodiment of the present invention. The dispenser 10 may be used to dispense a product 12 from a container 14. The product 12 may be a concentrated liquid, such as a cleaning or disinfecting product held in a container 14. Alternatively, the product 12 may be in the form of a powder or an aerosol. The product 12 in a powder form may be mixed with another liquid (e.g., water) prior to being dispensed. The product 12 may also be a solid (e.g., compacted into a tablet) which may then dissolve in a liquid solvent 16 prior to being dispensed. The container 14 can be a bottle, bag, box, bucket and the like. The product 12 may be dispensed via an outlet 18. In the embodiment shown in FIG. 3, the dispenser 10 includes a diluting solvent 16. The product 12 may be diluted by the solvent 16 and dispensed at the outlet 18. In other embodiments, the product 12 may be dispensed without being diluted. Typically, the solvent 16 can be water, and the dispenser 10 may be coupled to a water supply line (not shown).

The dispenser 10 generally includes a housing 20. The housing 20 may be portable or stationary with respect to a support surface (not shown) on which the dispenser 10 is positioned. The housing 20 may include one or more covers 40 and doors 36 to protect, store or limit access to the components of the dispenser 10. The cover 40 and door 36 may ensure that a user is not exposed to the product 12 inadvertently during use. Such embodiments may also ensure that the product 12 stored in the container 14 is not contaminated due to inadvertent exposure to surrounding conditions (e.g., particulates suspended in a room, dust, light, heat, etc.) The housing 20 may be free standing or may be designed to be mounted on a wall.

Figure 3:
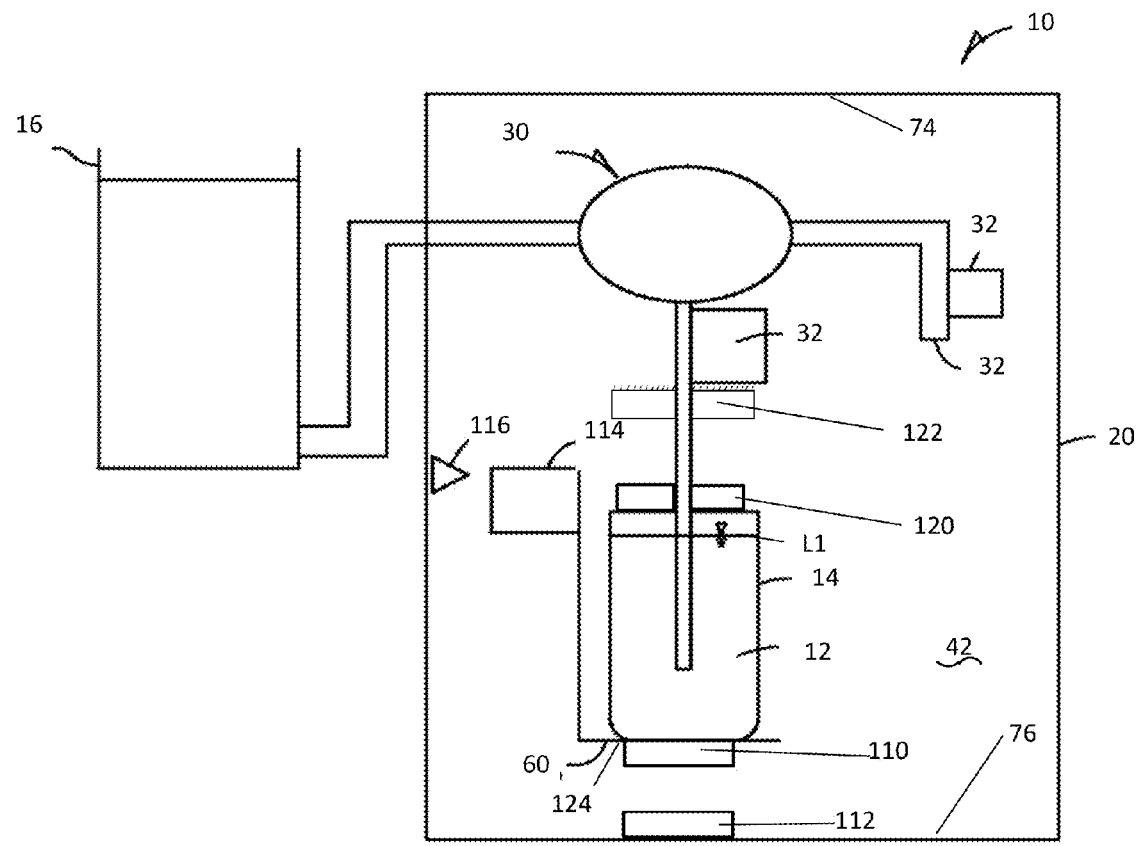
FIG. 3 is a schematic of the dispenser according to some embodiments with a product level at a maximum.
Figure 4:
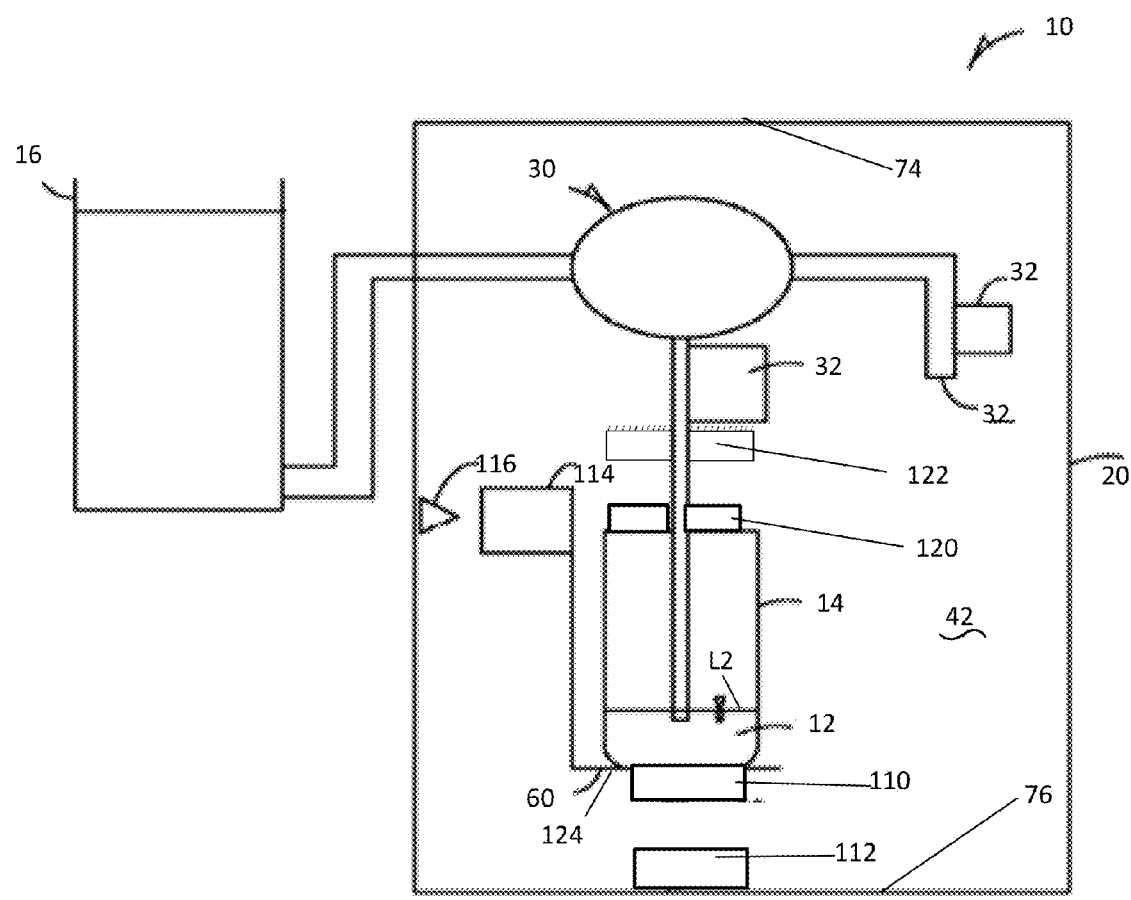
FIG. 4 is a schematic of the dispenser according to some embodiments with a product level at a low level.

In some illustrated embodiments shown in FIGS. 3 and 4, the container 14 may be connected with a manifold assembly 30. The manifold assembly 30 may facilitate removing the product 12 from the container 14 and supplying it to the outlet 18. Alternatively, or in addition, the manifold assembly 30 may facilitate diluting and/or dispersing the product 12 into an aerosol. A variety of manifold assemblies may be suitable for use with the dispenser 10 shown in FIGS. 3 and 4. For instance, a system and assembly for handling liquid products is disclosed in U.S. Provisional Patent Application No. 61/734,532, which is hereby incorporated by reference in its entirety. The manifold assembly 30 may include controls 32 for controlling the dispensing of product 12 from the dispenser 10.

The dispenser 10 may be well-suited for dispensing a cleaning and/or sanitizing product (e.g., concentrated peroxyacietic acid and hydrogen peroxide solution). The dispenser 10 can dispense a diluted solution to a bottle, a bucket or the like. FIG. 1 shows the dispenser 10 being configured to dispense the solution to a bottle 34. The dispenser 10 housing 20 is in the form of a cabinet intended to be mounted on a wall. The housing 20 may have a door 36 including a lock 38 as well as a cover 40. The door 36 may selectively open and close as seen in FIG. 2. When the door 36 is opened, it may provide access to the product storage area 42 (best seen in FIG. 2). The cover 40 may enclose and protect the manifold assembly 30 (best seen in FIGS. 3 and 4). The front of the housing 20 includes a recessed dispensing area 44 and an outlet tube 46 that extends downwardly from the manifold assembly 30 to provide an outlet 18 for the solution to be dispensed. A control, such as a button 48, can be used to activate and deactivate the dispensing of the solution. For instance, a user may position and align the bottle 34 in line with the outlet tube 46 and press the button 48 to dispense the solution into the bottle 34. Once a desired amount of solution has been dispensed in the bottle 34 the button 48 may be released to stop the dispensing process. Alternatively, a timer (not shown) may be coupled to the container and/or manifold assembly. The timer may facilitate timed dispensing of the product. For instance, the timer may be configured such that the product is dispensed for certain duration of time, after which, the dispensing may be turned off automatically. The timer may also be configured to begin dispensing after a certain interval of time.

While an exemplary product dispensing operation is described herein, other types of dispensing processes are contemplated. For instance, the dispenser described herein can dispense the product in an undiluted liquid, loose powder, compacted tablet and/or aerosol form. Instead of, or in addition to a manifold assembly, the dispenser may include an atomizer or nebulizer (not shown) to disperse the product in an aerosol form. As illustrated in FIGS. 1 and 2, the product 12 may be dispensed from the outlet 18 into the bottle 34 assisted by gravity. Other embodiments may include a pump, a nozzle and one or more flow metering apparatus (not shown) to dispense the product into the 34.

With continued reference to FIGS. 1 and 2, the dispenser 10 may include an adapter 50 stored within the recessed dispensing area 44. A bucket dispensing handle 52 may be releasably stored within a recess or in the cover 40. The bucket dispensing handle 52 is released from the cover 40 (e.g., from its retaining slot) within the recessed dispensing area 44. A hose 56 may extend from the lower portion of adapter 50, and pass through a passage in the lower portion of the housing and engages with the bucket dispensing handle 52. A retainer clip 58 may be used to connect the bucket dispensing handle 52 to the bucket (not shown). A user may then dispense solution into the bucket by activating the dispenser 10 using the button 48.

Figure 5:
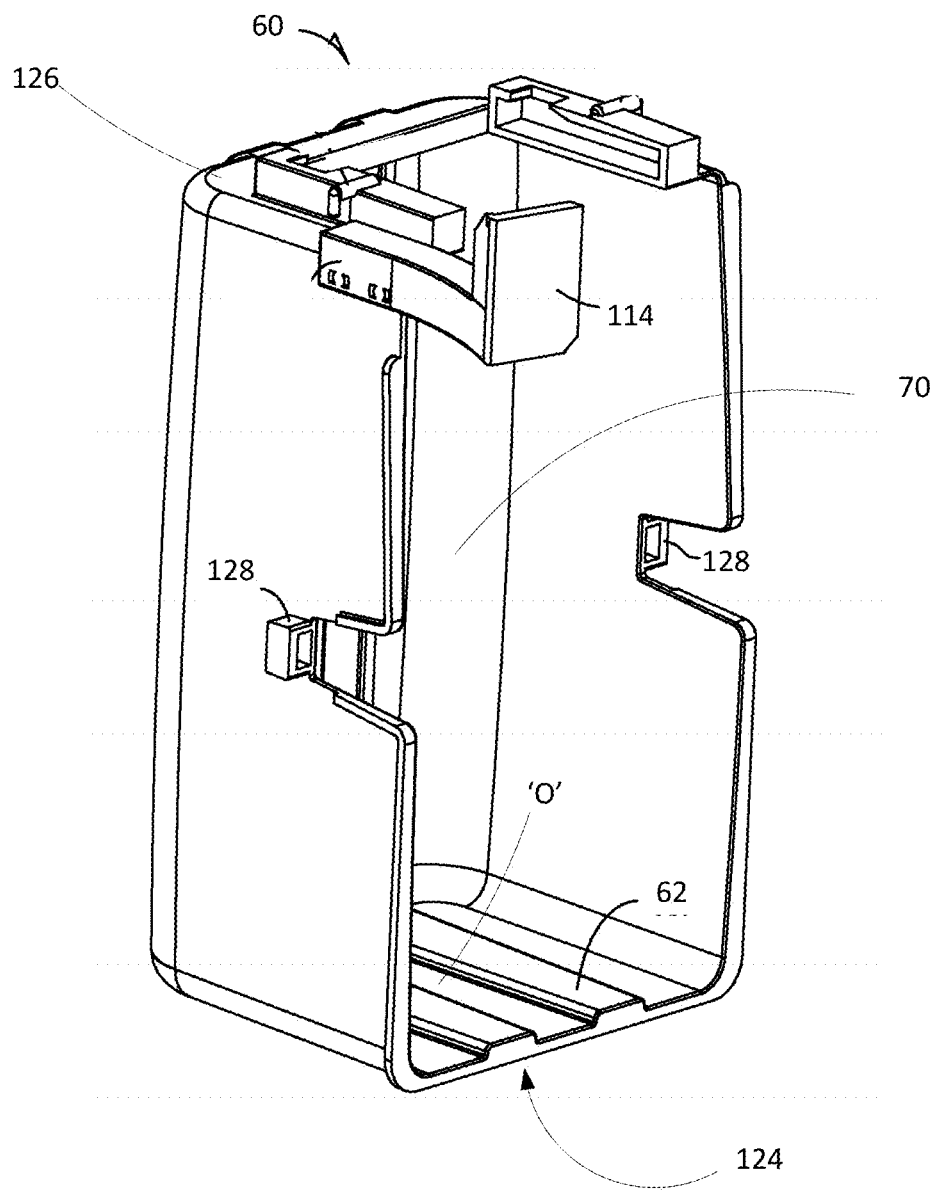
FIG. 5 is a detailed perspective view of a container holder of the dispenser of FIG. 1 according to some embodiments of the invention.

With continued reference to FIG. 2, the container 14 may be supported by a container holder 60 positioned within the housing 20. Details of the container holder 60 can best be seen in the perspective view of FIG. 5. The container holder 60 may include a support surface 62 for supporting the container 14. As seen in FIG. 2, the housing 20 may include recessed tracks 64 (e.g., rails, guides etc.) which may engage with mating tabs 128 (best seen in FIG. 5) of the periphery of the container holder 60. The recessed tracks may allow the container 14 to "ride" along the tracks (e.g., vertically upwards or downwards). In the illustrated embodiment shown in FIG. 2, one or more guides 68 are provided on the inner walls of the housing 20. The guides 68 may each form a channel. Tabs 128 positioned on the container holder 60 can be received within the channels defined by the guides. Once a tab is received within its corresponding channel the container holder 60 may move in a generally vertical direction over a predetermined distance. The tabs 128 retained within the channels of the guides 68 may also prevent transverse (e.g., forward and backward with respect to the back wall 70, best seen in FIG. 5), lateral (e.g., rightward and leftward with respect to the side wall 72) or rotational movement of the container holder 60. As the container holder 60 and the container 14 supported thereon may be made of plastics (e.g., molded from polymers such as PET plastic), the container 14 or the container holder 60 may not twist (e.g., rotational movement with respect to an axial face of the container 14 or container holder 60) when retained in the recessed tracks 64.

As a user operates the dispenser, a level of the product remaining within container may decrease. For products that are in the form of loose or compacted powder, the weight of the product may instead be used to determine if a sufficient quantity of product remains in the container. FIG. 3 illustrates the dispenser 10 wherein the product 12 is at a maximum level and/or weight 'L1'. FIG. 4 shows a schematic of the dispenser 10 wherein the product 12 is at a pre-determined minimum level and/or weight 'L2'. The container 14 may be completely empty when the dispenser 10 removes the product 12 from the container 14 beyond the predetermined minimum level and/or weight. Alternatively, the predetermined minimum level may correspond to a condition when the container 14 is substantially empty. It may often be beneficial to alert a user when the level or weight of the product 12 in the container 14 reaches a pre-determined minimum level. For instance, the pre-determined level may include a minimum level of the product 12 required to perform an operation (e.g., cleaning) with the product 12. It may also be beneficial to alert a user when the level of product remaining corresponds to a maximum level of the product that may remain in the container when disposing the product and/or recycling the container to comply with chemical safety regulations. Alerting the user may prevent delays or increased lead times in a dispensing operation, especially if a facility stocks only a limited quantity of product in its inventory. Accordingly, the dispenser of FIGS. 1-4 may be provided with a magnetic system to provide a user with that may allow the user to refill or replace the product before or when the container is empty. Further, as mentioned previously, regulatory requirements may determine a predetermined volume or concentration of the product be maintained in the container for effectively cleaning a facility and removing microorganisms.

Figure 6:
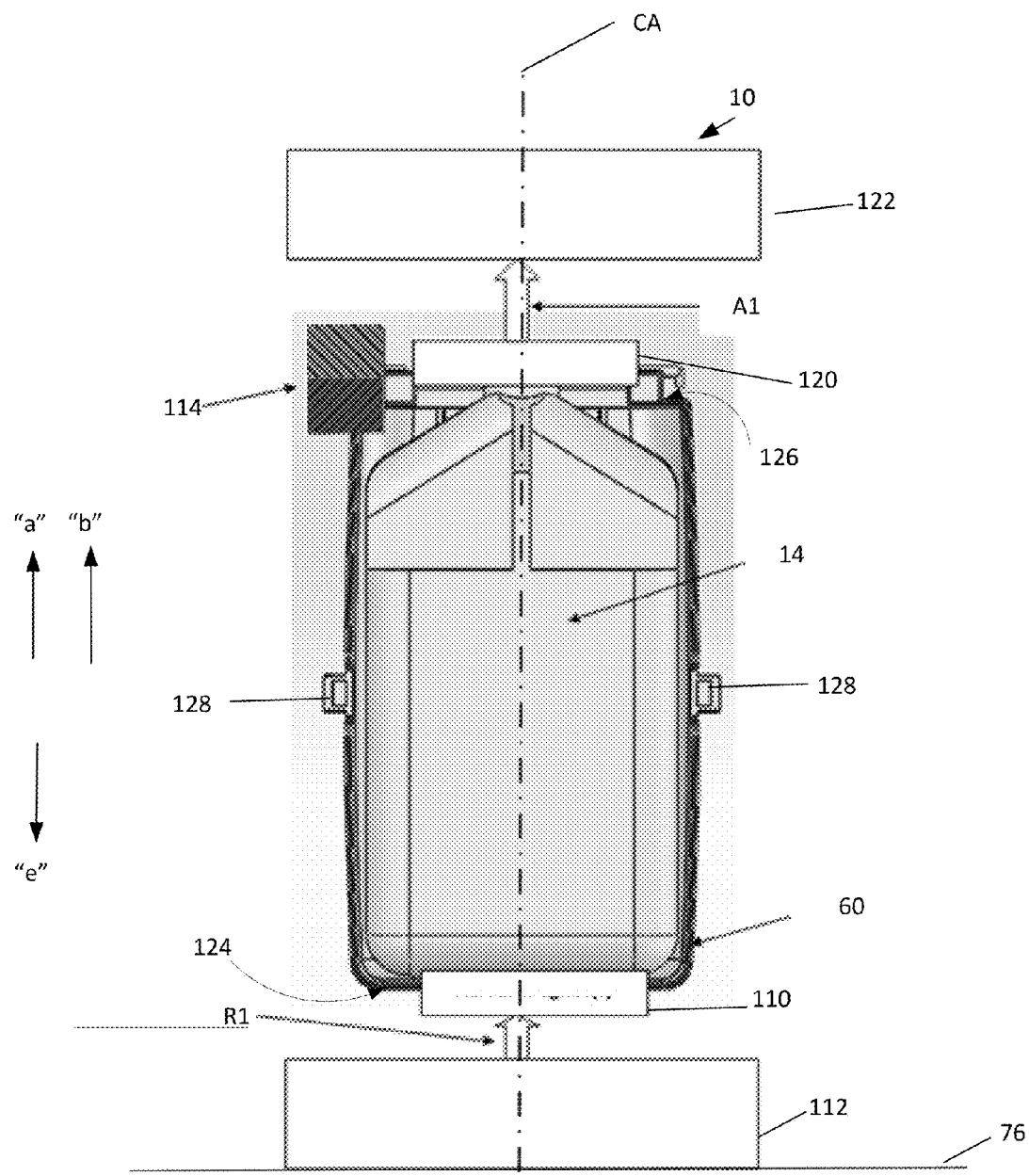
FIG. 6 is a schematic of a magnetic system coupled to a container holder of a dispenser according to some embodiments.

As seen in FIG. 6, the magnetic system 100 may include a first holder magnetic element 110 positioned on the container holder 60. The first holder magnetic element 110 may generate a first magnetic force due to magnetic interaction with a first stationary magnetic element 112 positioned external to the container holder 60, thereby inducing the container holder 60 to move along the container holder axis 'CA' in a first direction from an initial position. As the container holder 60 moves along the container holder axis 'CA', the container holder 60 may reach a final position at which point, an indicator 114 and/or a sign 116 may be activated or viewed to indicate that the weight of the product in the container has reached below a pre-determined weight.

With continued reference to FIG. 6, the container holder 60 may initially be at rest. In such an embodiment, the first magnetic force may act in a vertically upward direction "a," illustrated by the arrow in FIG. 6. The first magnetic force may be equal in magnitude and opposite in direction to the force acting in a vertically downward direction "e". The force acting in the vertically downward direction may be a sum of the weight of the product 12, the weight of the container 14, and the weight of the container holder 60. Alternatively, the weight of the container 14 and the container holder 60 may be compensated for such that the magnitude of the first magnetic force equals the weight of the product 12 when the container holder 60 is at rest. Thus, when the weight of the product 12 decreases, the vertically upward directed first magnetic force overcomes the vertically downward directed weight and the container holder 60 may start moving in an upward direction.

In another exemplary embodiment, the magnetic system 100 shown in FIG. 6 may be configured such that the first holder magnetic element 110 initiates movement of the container holder 60 when the weight of the product 12 in the container 14 is less than the first pre-determined weight of the product 12. In other words, the first magnetic force may not initiate movement when the product 12 is removed from the container 14 as long as the weight of the product 12 is greater than the first pre-determined weight. Although not illustrated, the following example may illustrate the operation of the magnetic system in accordance with an embodiment. The container may initially have 3000 grams of a product. The first magnetic force may not induce movement until the weight of the product in the container is 150 grams. The movement of the container holder may actuate the indicator to provide a first indication to a user. The first indication may inform the user that the weight of the product in the container is below the first-predetermined weight, i.e., 150 grams.

The first holder magnetic element may be a programmable magnet. Such programmable magnets allow a user configure the first holder magnetic element such that the force response of the magnet can be controlled. An exemplary programmable magnet is described in U.S. application Ser. No. 13/687,819 assigned to Correlated Magnetics, the disclosure of which is hereby incorporated by reference in its entirety. In an exemplary embodiment seen in FIG. 6, a user may configure the first holder magnetic element 110 such that the first magnetic force R1 is a repellant force. The first magnetic force R1 can be configured to move the first holder magnetic element 110 away from the first stationary magnetic element 112. Additionally, the user may be able configure the first holder magnetic element 110 such that the first magnetic force R1 is of a pre-determined magnitude.

Figure 7A:
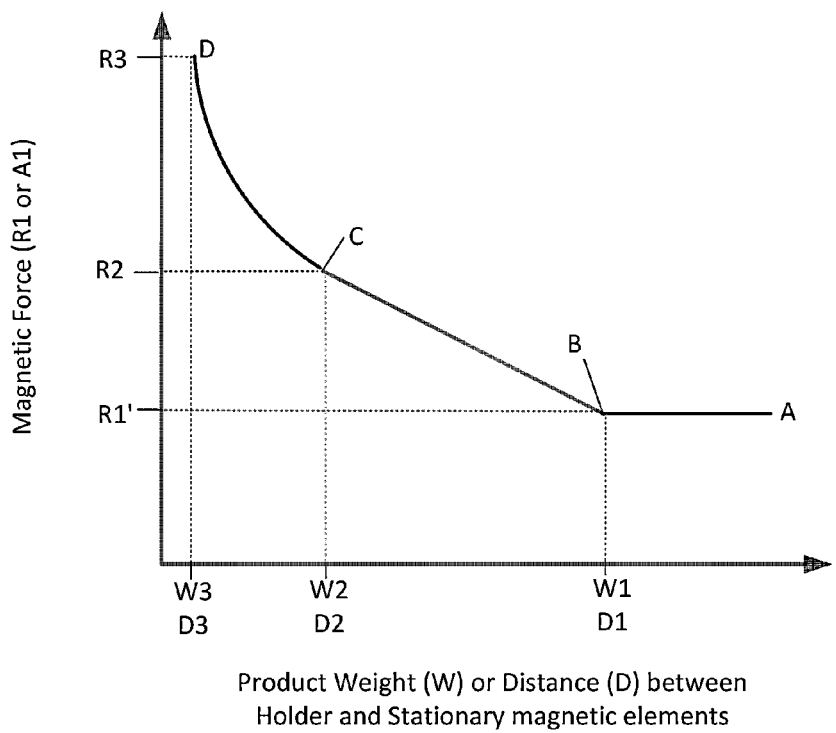
FIGS. 7A and 7B are force response curves of the magnetic system according to some embodiments.
Figure 7B:
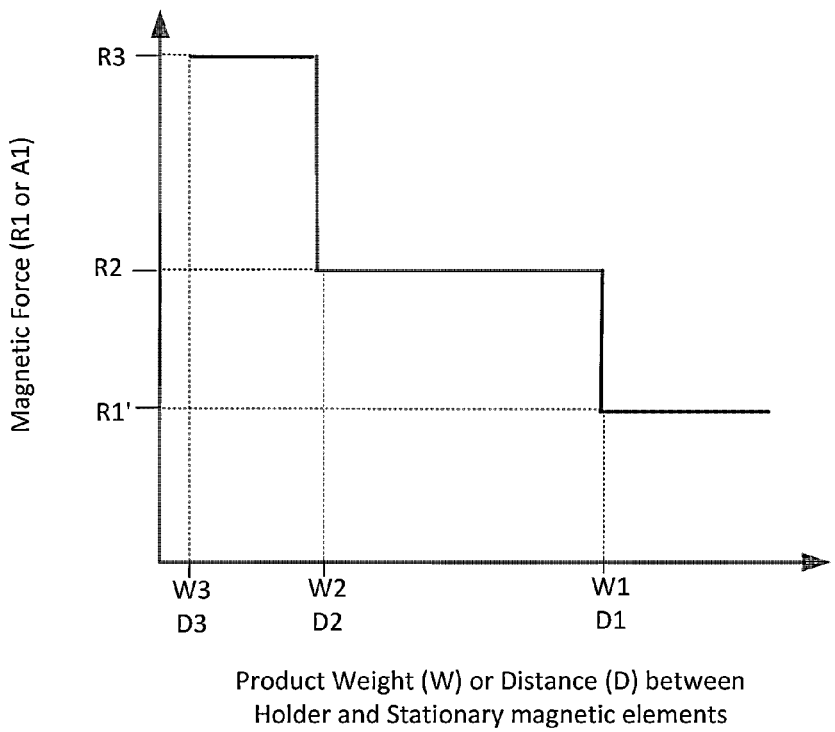

As illustrated in FIGS. 7A and 7B, during manufacturing, or in use, the first holder magnetic element 110 may be programmed to have a pre-determined force response based on a distance between the first stationary magnetic element 112 and the first holder magnetic element 110. In a non-limiting exemplary embodiment, the first holder magnetic element 110 can be configured such that the first magnetic force R1 is linearly proportional to the distance between the first holder magnetic element 110 and the first stationary magnetic element 112 as seen by the Portion B-C of FIG. 7A. In other embodiments, the first magnetic force R1 may vary non-linearly with the distance between the first holder magnetic element 110 and the first stationary magnetic element 112 as seen by the Portion C-D of FIG. 7A. For instance, the first holder magnetic element 110 may be programmed such that the first magnetic force R1 varies exponentially with the distance between the first stationary magnetic element 112 and the first holder magnetic element 110. While the embodiments disclosed herein include a first magnetic force that is repellant (i.e., adapted to move the first holder magnetic element 110 and first stationary magnetic element 112 away from each other), the first magnetic force may instead be an attractive force configured for moving the first holder magnetic element 110 and first stationary magnetic element 112 toward each other.

As seen in FIG. 7B, the first holder magnetic element can be configured such that the first holder magnetic element and the first stationary magnetic element generate a first repellant magnetic force R1' when it is at a first distance D1 from the first stationary magnetic element, and a second repellant magnetic force R2 when it is at a second distance D2 from the first stationary magnetic element. The first and second distances D1, D2 can be correlated with the weight of the product remaining in the container W1, W2. In other words, the first holder magnetic element and the first stationary magnetic element may be separated by the first distance when the weight of the product in the container is above the first pre-determined weight. At this position, the magnetic force generated due to interaction of the first holder magnetic element and the first stationary magnetic element may equal the first repellant magnetic force R1. As the dispenser continues to dispense the product, the weight of the product in the container drops below the first pre-determined weight W1 and the container may start moving vertically upward due to force R2. As the first holder magnetic element is positioned on the container holder, and the first stationary magnetic element is positioned external to the container holder, the distance between the first holder magnetic element and the first stationary magnetic element may change as the container holder continues moving vertically upward. In some instances, when the weight of the product falls below a second pre-determined weight W2 (less than the first predetermined weight), the first holder magnetic element and the first stationary magnetic element may be separated by the second distance D2, at which point, the magnetic force between the first holder and stationary magnetic element may equal the third repellant magnetic force R3 on the first stationary magnetic element.

In a non-limiting exemplary embodiment shown in FIG. 7A, the first repellant magnetic force R1' may induce a movement of the container holder, such that the distance between the first holder magnetic element and the first stationary magnetic element varies linearly with the weight of the product remaining in the container. This linear movement may continue until the weight of the product is below the first pre-determined weight W1, but above a second pre-determined weight W2. The first holder magnetic element may be configured such that the magnetic force created by the interaction of the first holder magnetic element and first stationary magnetic element varies linearly with weight of the product in the container until the weight of the product reaches the second pre-determined weight, below which the force created by the interaction of the first stationary magnetic element and the first holder magnetic element varies non-linearly with weight of the product in the container. This non-linear variation may be an exponential, a stair-step or a polynomial variation. Other non-linear relation between force of the first magnetic element and the weight of the product remaining in the container can also be contemplated. For instance, as the dispenser continues dispensing the product out of the container, the weight of the product may reach below the second pre-determined weight W2. Once the weight of the product reaches below the second pre-determined weight W2, the second repellant magnetic force R2 may be generated, which varies non-linearly with the weight of the product remaining in the container. Thus, if the dispenser continues to dispense the product, further decrease in weight of the product in the container may be accompanied by a non-linear force response. If, for instance, the weight of the product in the dispenser reaches below a third pre-determined weight W3 (less than the second pre-determined weight), a third repellant magnetic force R3 may be generated as a result of interaction between the first holder magnetic element and the first stationary magnetic element. The relationship between forces R2 and R3 is non-linear when the weight is between W2 and W3. While a repellant force is created by the interaction of the first holder magnetic element and the first stationary magnetic element in the embodiments described above, the first holder magnetic element and/or the first stationary magnetic element can magnetically interact to generate a repellant or an attraction force.

While the embodiments described above relate to the variation of magnetic force of the first magnetic element based on weight of the product, it can be seen that the first holder magnetic element may be programmed such that the variation of magnetic force of the first holder magnetic element is with respect to the distance between the first holder magnetic element and the first stationary magnetic element, as shown in FIGS. 7A and 7B. In other words, the first holder magnetic element may be configured such that the magnetic force due to the interaction of the first holder magnetic element and the first stationary magnetic element varies linearly with distance between the first holder magnetic element and the first stationary magnetic element until the second distance D2, above or below which, the magnetic force created by the interaction of the first holder magnetic element and the first stationary magnetic element varies non-linearly with distance between the first holder magnetic element and the first stationary magnetic element. The embodiments described thus far relate to the first holder magnetic element being configurable to have a desired force in response to weight of the product in the container or the distance between the first holder magnetic element and the first stationary magnetic element. However, other variations are also within the scope of the disclosure. For instance, instead of the first holder magnetic element, the first stationary magnetic element may be programmable such that during manufacturing, or in use, the force response of the first stationary magnetic element is programmed with respect to the weight of the product in the container or the distance between the first holder magnetic element and the first stationary magnetic element. Alternatively, each of the first holder magnetic element and the first stationary magnetic element may be programmable such that the force response of each of the first holder magnetic element and the first stationary magnetic element is programmed during manufacturing or in use.

Referring back to FIG. 6, the dispenser 10 may include a second holder magnetic element 120 positioned on the container holder 60. The second holder magnetic element 120 may also be a programmable magnetic element. The second holder magnetic element 120 may be programmed so as to interact with a second stationary magnetic element 122 and generate a second magnetic force according to the force responses shown in FIGS. 7A and 7B. The second magnetic force may be an attraction or a repellant force. As seen in FIG. 6, the second stationary magnetic element 122 may be positioned external to the container holder 60. The second magnetic force may induce the container holder 60 to move along the container holder axis 'CA' in a second direction "b". In a non-limiting exemplary embodiment, the first and second directions can be parallel to a vertically upward direction. Although not illustrated, the first and second directions may also be oriented such that they are disposed at an angle with respect to the container holder axis 'CA'.

With continued reference to FIG. 6, the first magnetic force can be a repellant force between the first holder magnetic element 110 and the first stationary magnetic element 112. In such embodiments, the second magnetic force can be an attraction force between the second holder magnetic element 120 and the second stationary magnetic element 122. In such embodiments, the second magnetic force may assist the first magnetic force in moving the container holder 60 vertically upwards. The first and second holder magnetic elements 110, 120 and/or the first and second stationary magnetic elements 112, 122 may be programmed to achieve a desired force response (as illustrated in FIGS. 7A and 7B) that moves the container 14 in a preferred direction to a preferred position. In a non-limiting exemplary embodiment shown in FIG. 6, the first and second holder magnetic elements 110, 120 and/or the first and second stationary magnetic elements 112, 122 may be positioned such that the first repellant magnetic force R1 and the second attraction A1 magnetic force are both oriented in a vertically upward direction. The first repellant magnetic force R1 may initially move the container holder 60 in a vertically upward direction until the distance between the second holder magnetic element 120 and the second stationary magnetic element 122 reaches a preset value. At this distance, the second holder magnetic element 120 and/or the second stationary magnetic element 122 may act on each other (e.g., via second attraction force) to further move the container holder 60 in a vertically upward direction. The increased magnetic forces due to the attraction and the repellant forces A1, R1 being oriented in the same direction may lead to a rapid movement of the container holder 60. As will be discussed below, such rapid movement may effectively caution a user that the product in the container has reached a minimum threshold level (e.g., first, second or third predetermined weights). Further, the magnets may be programmed such that the force response of each of the first and second holder magnetic elements and first and second stationary magnetic elements may be independently "tuned" such that a desired movement of the container holder and a concomitant indication is provided to the user regarding the weight and/or level of the product remaining in the container.

As seen by the schematic in FIG. 6, the second holder magnetic element 120 and the second stationary magnetic element 122 may be substantially similar to the first holder magnetic element 110 and first stationary magnetic element 112 respectively, in size, shape, configuration, magnetic field strength, magnetic force and the like, but of opposite polarity. The magnetic polarity (not shown) of the holder magnetic elements and stationary magnetic elements may be configured such that the second holder magnetic element 120 and/or the second stationary magnetic element 122 may interact to generate an attraction force A1, and the first holder magnetic element 110 and/or the first stationary magnetic element 112 may interact to generate a repellant force R1. In alternate embodiments, the polarity of the second holder magnetic element 120 and/or the second stationary magnetic element 122 may be configured such that the second holder magnetic element 120 and/or the second stationary magnetic element 122 may repel each other at certain distances between them, and may reverse polarity to attract each other at certain other distances between them. For instance, the second holder magnetic element 120 and/or the second stationary magnetic element 122 may repel each when the distance between them is greater than a predetermined "repel distance," (not shown) and may attract each other when the distance between them is less than the pre-determined repel distance.

Alternatively, the second holder magnetic element and/or the second stationary magnetic element may repel each other when oriented at a given angular orientation with respect to each other. When the angular orientation of the second holder magnetic element and/or the second stationary magnetic element changes (e.g., rotation by a mechanical key, gears, or similar drive means), the polarity may be altered such that the second holder magnetic element and/or the second stationary magnetic element attract each other. Alternatively, the second holder magnetic element and/or the second stationary magnetic element may repel each other when oriented at a given lateral position with respect to each other (e.g., the centers of the second stationary magnetic element and the second holder magnetic element not in line with each other in the rightward-leftward plane) and may attract each other when brought in line laterally.

Alternatively, the second holder magnetic element and/or the second stationary magnetic element may repel each other when oriented at a given transverse position with respect to each other (e.g., the centers of the second stationary magnetic element and the second holder magnetic element not in line with each other in the forward-backward plane) and may attract each other when brought in line transversely. Any combination of the above embodiments is also contemplated. While the embodiments described thus far relate to programmable force response of the second holder magnetic element and/or the second stationary magnetic element with respect to their longitudinal, lateral and transverse positioning and rotational orientation, the first holder magnetic element and/or the first stationary magnetic element may also be programmable with a force response based on their longitudinal, lateral and/or transverse position and the rotational orientation. Further, force response as used herein may refer to change in the magnitude or the direction of the attraction or repellant forces in response to weight of the product in the container, distance between holder magnetic elements and stationary magnetic elements, position or orientation of holder magnetic elements and/or stationary magnetic elements.

Figure 8:
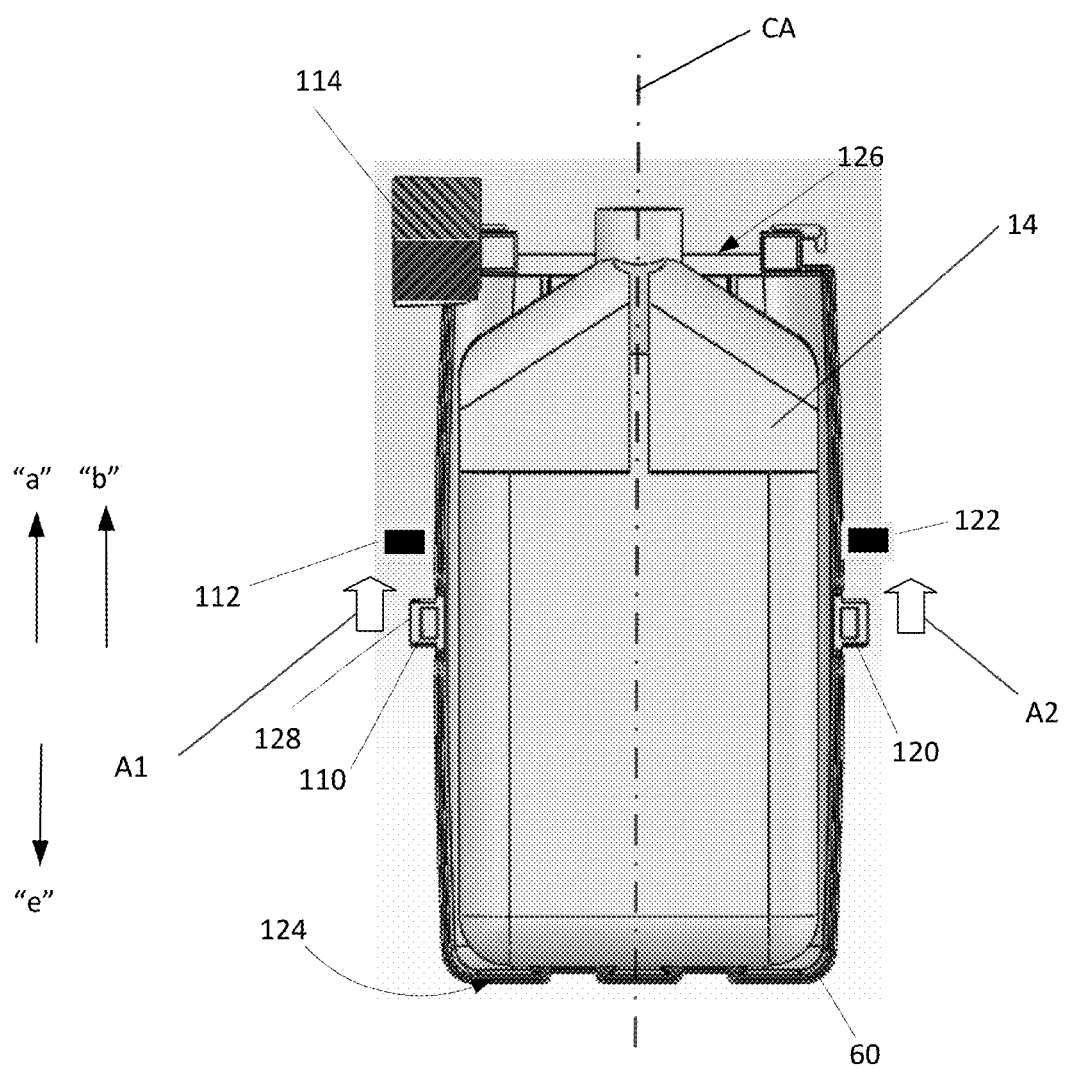
FIG. 8 is a schematic of a magnetic system coupled to a container holder of a dispenser according to some embodiments.

As shown in FIG. 6, the first stationary magnetic element 112 can be positioned axially opposite to the second stationary magnetic element 122. The first holder magnetic element 110 can be positioned on a first axial face 124 (best seen in FIG. 3) of the container holder 60 and the second magnetic element can be positioned on a second axial face 126 of the container holder 60. In the illustrated embodiment, the second axial face 126 (best seen in FIG. 5) is axially opposite to the first axial face 124. The first and second holder magnetic elements 110, 120 may instead be positioned peripherally on the container holder 60 as shown in FIG. 8. For instance, the first and second magnetic elements may be positioned on the top and bottom surfaces of the tabs 128 of the container holder 60. In such embodiments, in addition to the first and second magnetic elements, third and fourth magnetic elements (not shown) may be provided on a tab 128. Alternatively, the holder magnetic elements 110, 120 may be embedded within the tabs as shown in FIG. 8. In such embodiments, both the first and second holder magnetic elements 110, 120 and the first and stationary magnetic elements 112, 122 can interact to generate attraction forces A1, A2. However, the first and second holder magnetic elements 110, 120 may both be configured to interact with the first and second stationary magnetic elements 112, 122 to generate a repellant force if the first and second stationary magnetic elements 112, 122 are positioned below the tabs 128 shown in FIG. 8. The container holder 60 may include one or more arms (not shown) peripherally extending therefrom. The first, second, third and fourth magnetic elements may be positioned on the arms of the container holder 60. Alternatively, the container holder 60 may include a flared portion (e.g., a flange, not shown) for supporting one or more magnetic elements (e.g., six or eight magnetic elements, or a single annular magnet). Any number of holder magnetic elements with respective stationary magnets can be used without departing from the scope of the invention. The holder magnetic elements 110, 120 can be positioned on any vertex, edge or surface the container holder 60. The holder magnetic elements may, be placed on an interior surface or an exterior surface of the container holder 60.

Figure 9:
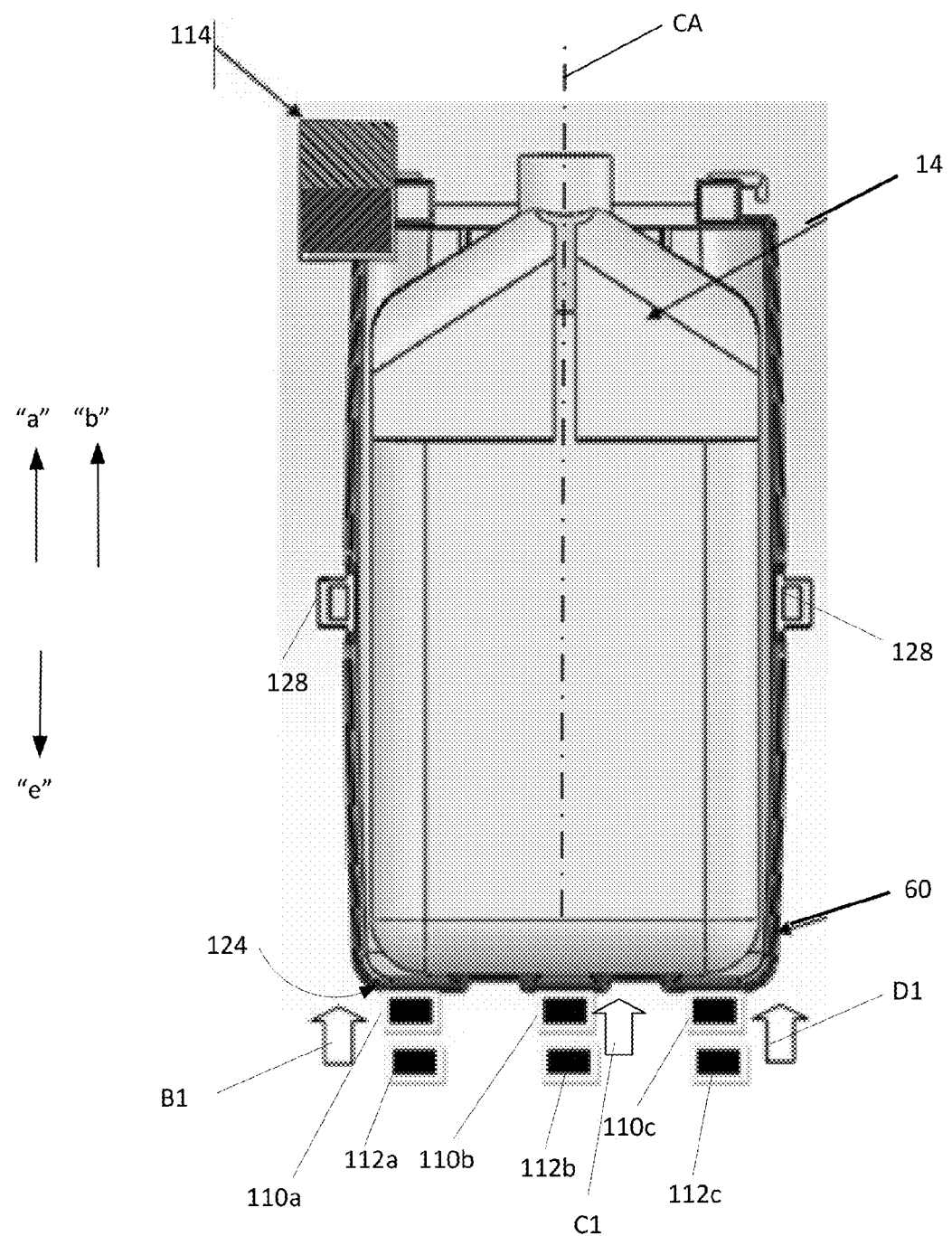
FIG. 9 is a schematic of a magnetic system coupled to a container holder of a dispenser according to some embodiments.

An exemplary embodiment illustrated in FIG. 9 shows three holder magnetic elements 110a, 110b and 110c and three stationary magnetic elements 112a, 112b, and 112c. In alternate embodiments seen in FIGS. 3 and 4, one or more of the holder magnetic elements 110, 120 may be positioned on opposing axial faces of the container 14 instead of the container holder 60. In the embodiment shown in FIGS. 3 and 4, the second holder magnetic element 120 is positioned on the container 14, while the first holder magnetic element 110 is positioned on the first axial face 124 of the container holder. Such embodiments may be well-suited if the container 14 were a reusable container so that the container 14 may be rinsed and/or reused once the container 14 is empty or when the remaining product is flushed-out. Such embodiments may also be suited when the holder magnetic elements include permanent magnets that retain their magnetic properties over several years/several use cycles of the dispenser. In such embodiments, the container holder 60 may be eliminated altogether from the dispenser 10, and the container 14 may move along a container axis (parallel to the container holder axis) due to the magnetic force.

Each of the holder magnetic elements and stationary magnetic elements may comprise a single magnet (110, 112, 120, 122) as seen in FIGS. 6 and 8 or a plurality of magnets (110a, 110b, 110c and 112a, 112b and 112c) as seen in FIG. 9. The first and second holder magnetic elements 110, 120 and first and second stationary magnetic elements 112, 122 can be of any size or shape. The holder magnetic elements and stationary magnetic elements may each be a solid disc-shaped, block-shaped, cylindrical, spherical, triangular, tetrahedral, star-shaped, arcuate or horse-shoe shaped magnet disposed in line with the container holder axis 'CA'. Alternatively, the magnetic elements and stationary magnetic elements can be annular or ring-shaped magnets. For instance, the first holder magnetic element 110 may include three holder magnets positioned axially on the container holder 60 as seen in FIG. 9. The first stationary magnetic element 112 may either be a single magnet (as seen in FIG. 6), or may include three stationary magnets 112a, 112b, 112c (as seen in FIG. 9) positioned external to the container holder 60. Each of the three holder magnets 110a, 110b, and 110c may interact with each of the stationary magnetic elements 112a, 112b and 112c to generate a magnetic force B1, C1 and D1 (shown in FIG. 9) respectively. The magnetic forces B1, C1 and D1 are of a magnitude less than that of the first magnetic force R1 of the first holder magnetic element 110 (shown in FIG. 6). However, the sum of magnetic forces B1, C1, D1 may equal the first magnetic force R1. Each of the three holder magnets 110*a*, 110*b* and 110*c* shown in FIG. 9 may also be of smaller size than the single magnet 110 of FIG. 6 configured for generating an equivalent magnitude of magnetic force. Such embodiments may reduce the overall cost of the dispenser, as a plurality of smaller magnets may cost less than a single larger magnet.

As seen in FIGS. 6, 8 and 9, the first and second holder magnetic elements 110, 120 can be positioned on any surface of the container holder 60. For instance, if the container holder 60 is box shaped, the first holder magnetic element 110 can be positioned on corners of the first or second axial faces 124, 126. Such embodiments are especially well-suited if the holder magnetic elements include a plurality of magnets. For instance, if the first holder magnetic element 110 includes four magnets (not illustrated), they may be positioned on the vertices of the bottom surface of the box-shaped container holder. Alternatively, the first and second holder magnetic elements 110, 120 may be positioned centrally on an axial face (126 or 128) of the container holder 60. For instance, the first holder magnetic element 110 may be positioned on an axial face (126 or 128) of a cylindrical container holder, such that the center of the magnetic element coincides with a center 'O' (best seen in FIG. 5) of the axial face of the container holder 60. Such embodiments are especially well suited if the holder magnetic elements are singular magnets either solid or annular in shape. While the examples illustrate positioning of the first holder magnetic element 110 on the container holder 60, the examples can be readily extended to include positioning of the second holder magnetic element 120 on the container holder 60.

The first and second holder magnetic elements 110, 120 and first and second stationary magnetic elements 112, 122 may be made of any type of magnetic material (e.g., ferromagnetic, ferrites, rare-earth magnets etc.). The magnets may be made of materials such as iron, cobalt, nickel and their alloys (e.g., alnico or Aluminum nickel cobalt alloy), oxides (e.g., iron oxide compounds), neodymium, neodymium iron boron, samarium-cobalt compounds and the like. The first and second holder magnetic element 110, 120 and first and second stationary magnetic elements 112, 122 may be permanent magnets or temporary magnets that are temporarily actuable to generate a magnetic force. For instance, a material that exhibits electromagnetic properties when an electric current passes through it (e.g., an electromagnetic coil) may be used instead of magnets. Alternatively, one of the second holder magnetic element 120 and the second stationary magnetic element 122 may be a ferromagnetic material. In other words, the second holder magnetic element 120 or the second stationary magnetic element 122 may include non-magnetized materials that may be attracted by a magnet (e.g., iron and its alloys, iron oxides, etc.). In such embodiments, the other of the second holder magnetic element 120 and the second stationary magnetic element 122 may be a magnet configured for attracting the non-magnetized material.

Referring back to FIG. 6, the first and second stationary magnetic elements 112, 122 may be positioned in the housing 20 external to the container holder 60. For instance, the first and second stationary magnetic elements 112, 122 may be positioned on the top and bottom walls (74 and 76), respectively, of the product storage area 42 shown in FIG. 2. Alternatively, the first and stationary magnetic elements may be positioned within the product storage area 42, but supported by other surfaces (as shown in FIGS. 3 and 4). The location of the first and second stationary magnetic elements 112, 122 does not limit the scope of the invention and other locations can be readily contemplated by a skilled person.

Referring back to FIGS. 6 and 8, the dispenser 10 may include an indicator 114 to provide an indication to a user when a weight of the product 12 in the container 14 is below a first pre-determined weight of the product 12. While not illustrated in FIGS. 6 and 8, the indicator may provide a second indication to the user when the weight of the product 12 in the container 14 is less than a second pre-determined weight of the product 12. The indicator may further be configured to provide any number of indications desired by the user that corresponds to a predetermined weight of the product remaining in the container. The indicator 114 may be configured such that it provides an indication when the container holder 60 is at a first axial location (e.g., when the weight of the product 12 is below a first predetermined weight). The indicator may be configured such that it provides any number of indications to a user when the container holder 60 is at any of the possible axial locations (e.g., when the weight of the product is below a second predetermined weight, when the container is full, when the container is empty, etc.). The indicator 114 may be correlated with the holder magnetic elements 110, 120, such that the holder magnetic elements 110, 120 actuate the indicator 114 when an indication is desired. For instance, the indicator 114 may provide an indication when the weight of the product reaches a predetermined weight, or when the container holder reaches a certain position due to the magnetic force being greater than the weight of the product remaining in the container, as described with respect to various embodiments disclosed herein. Thus, a user may know the level or weight of the product remaining in the container in advance and may begin sourcing replacement when needed.

Figure 10:
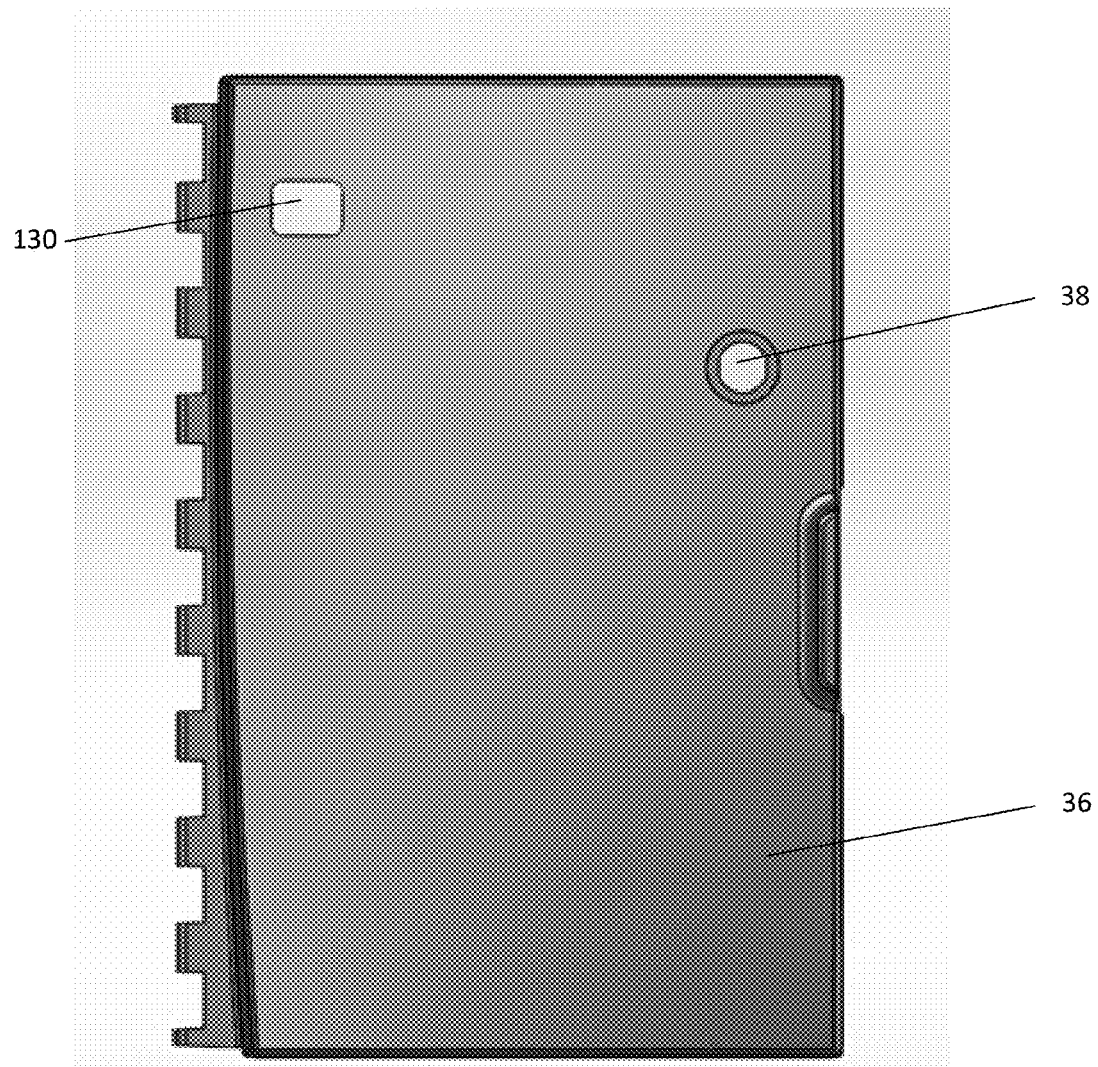
FIG. 10 is a front view of a door with an indicator window according to some embodiments.
Figure 11:
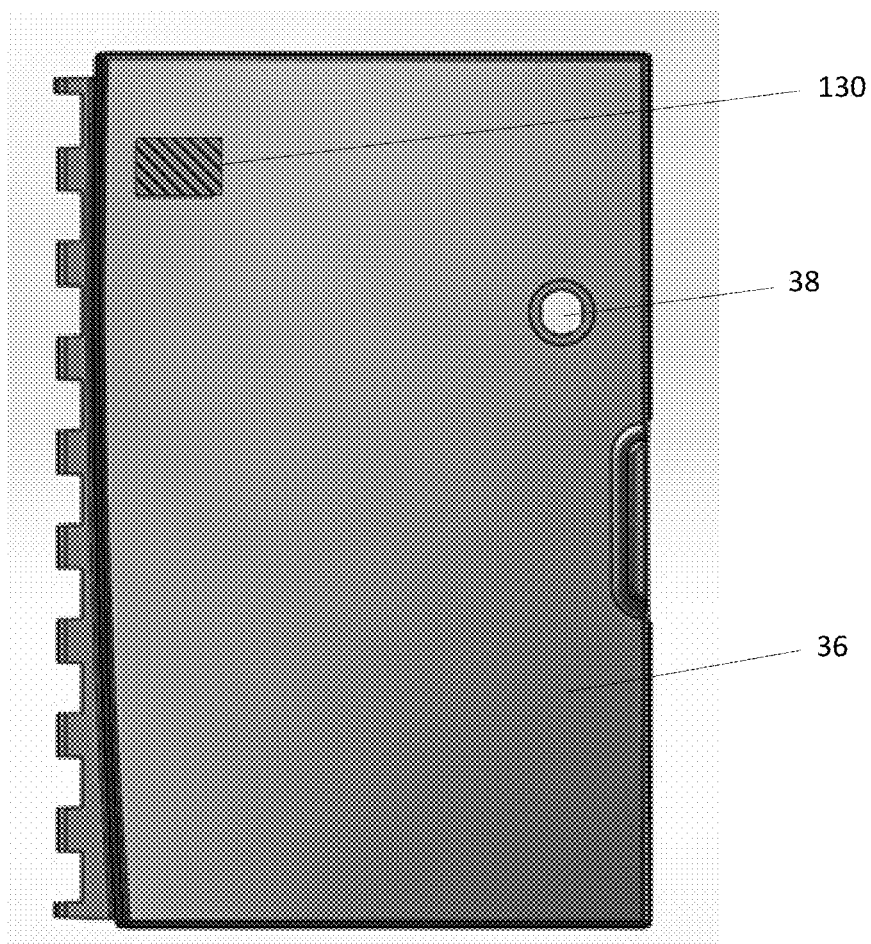
FIG. 11 is a front view of the door of FIG. 10 with a first pattern in line with the indicator window.
Figure 12:
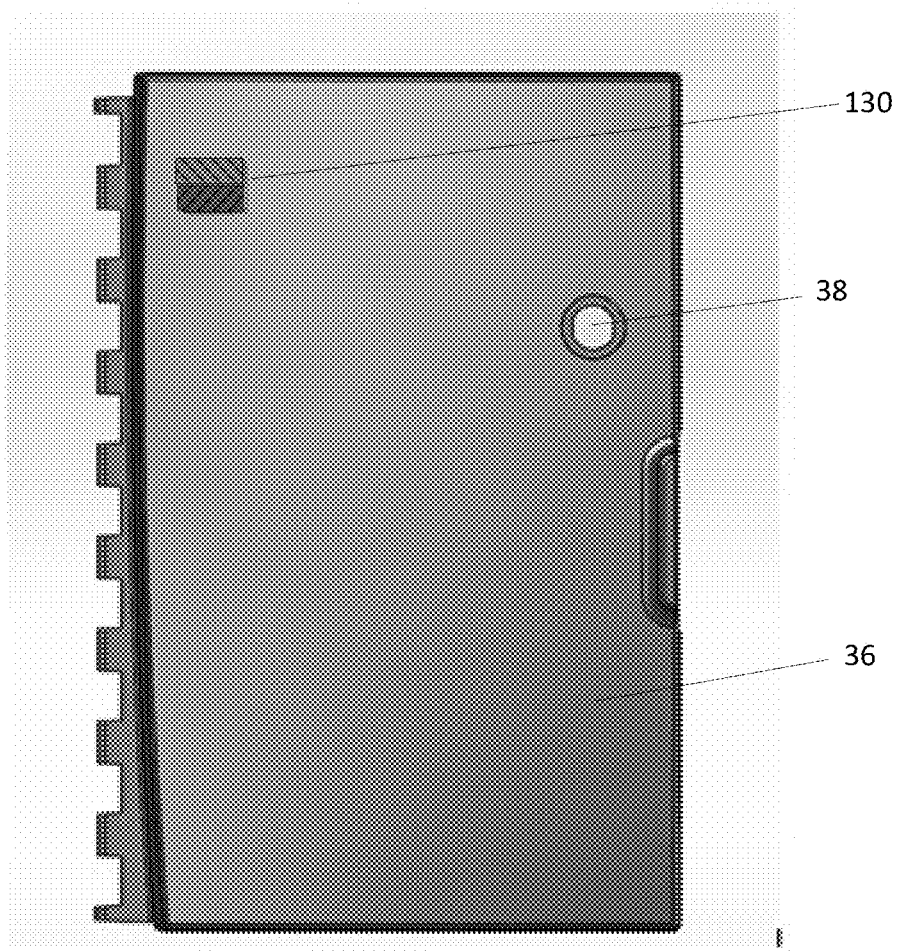
FIG. 12 is a front view of the door of FIG. 10 with a second pattern partially in line with the indicator window.
Figure 13:
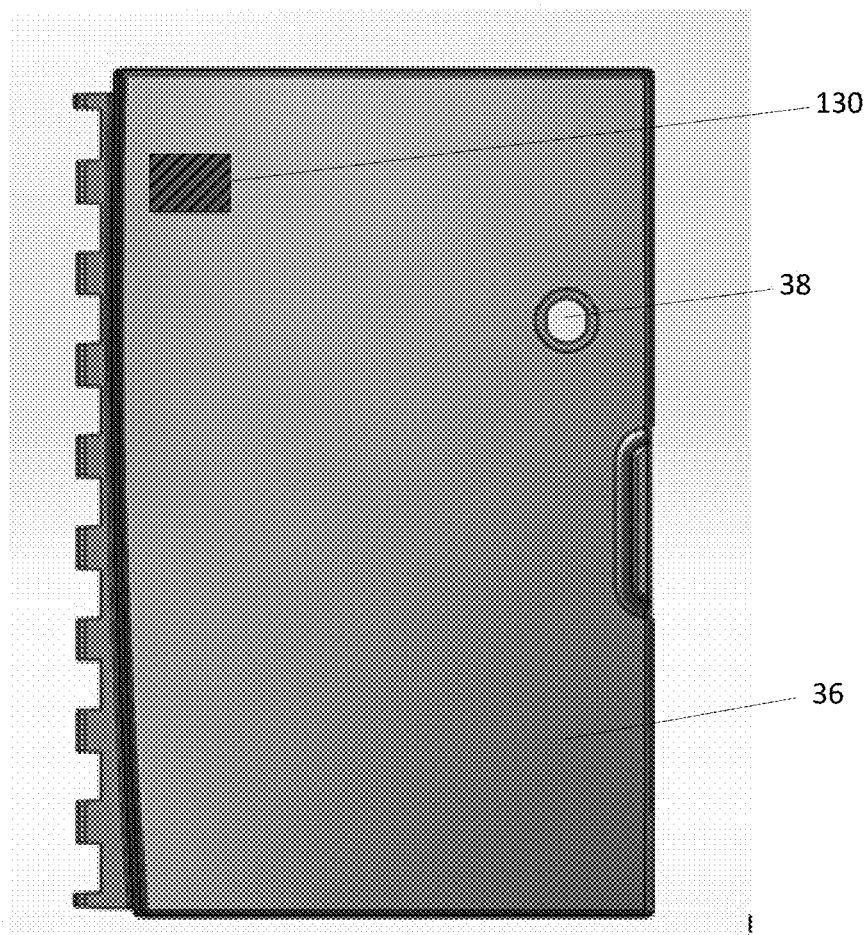
FIG. 13 is a front view of the door of FIG. 10 with the second pattern completely in line with the indicator window.

As seen in FIGS. 1 and 10, an indicator window 130 can be provided on the door 36 to facilitate a visual alert. A user may then simply look through the indicator window 130 to discern the level or weight of the product in the container. As seen in FIGS. 11-13, the indicator 114 may include a colored or patterned area. As seen in FIG. 11, the indicator 114 may include a green area or a first pattern in alignment with the indicator window 130 when the container is full. The indicator may include a yellow area or a second pattern (not shown) vertically below the green area. As the product is dispensed, the magnetic forces move the container vertically upwards, resulting in aligning the yellow area with the indicator window 130. The magnetic force may be configured to move the container to a desired position when the weight of the product reaches or is below a predetermined weight, such that the yellow area may align with the indicator window 130. The holder magnetic elements and the stationary magnetic elements may be programmed based on factors such as minimum weight of the product that must be maintained in the container at all times, maximum weight of the product that a container may store when the container is recycled and/or the product is disposed, safety regulations and standard operating procedures for a particular facility where the dispenser is used. Similarly, as shown in FIG. 12, the indicator may include a red area or a third pattern below the green area, which may be brought into alignment with the indicator window 130 due to magnetic forces when the container is substantially empty and/or need immediate replacement. While an exemplary three color indication scheme is illustrated, the first and second holder magnetic elements and the first and second stationary magnetic elements may be configured for providing any number of indications.

As illustrated by the drawing FIGS. 6, 8 and 9, in addition to the first and second holder magnetic elements 110, 120 positioned on axially opposite faces 124, 126 of the container holder 60, the container holder 60 may include additional magnetic latches (not shown) positioned on the side of the container holder 60. The magnetic latches may latch to certain locations of the housing 20. The magnetic latches on the side may initially fix the position of the container holder 60, and as the dispenser 10 continues to dispense the product 12, the magnetic latches may release the container holder 60 because of the first and/or second holder magnetic element 110, 120 positioned on the axial faces 124, 126 of the container holder 60 may interact with first and/or second stationary magnetic elements to generate magnetic forces that overcome latching force of magnetic latches. While magnetic latches may be well-suited, any latch (e.g., a mechanical latch, an electrical latch and the like) may be provided. Such latches may be provided at various axial locations on the container holder 60, so as to enable latching/releasing of the container holder 60 as the container holder 60 moves vertically upwards (i.e., at different axial positions of the container holder 60 corresponding to different weights of product 12 remaining in the container 14).

In some embodiments, instead of or in addition to a magnetic latch, an electrical latch (e.g., an electrical circuit not shown) may be coupled to the indicator. The electrical circuit may be operatively coupled to the first and second holder magnetic elements and first and second stationary magnetic elements such that when the container is completely empty, one of the first and second magnetic elements may close the electrical circuit, resulting in an alert system. The alert may be a visual alert such as a light coupled to the electrical circuit which glows when the electrical circuit is closed (e.g., a red LED lamp), or an audio alert (e.g., an alarm sound). Alternatively, the holder magnetic elements and stationary magnetic elements may not completely close the circuit, but remain proximal to the electrical circuit. In such embodiments, one or more of a reed switch, a Hall-effect sensor, a proximity sensor, an infrared switch, an optical switch, or a contact switch may activate the electrical circuit based on the position of first and/or second magnetic elements or first and/or second stationary magnetic elements. As the electrical circuit is triggered, an LED lamp, a display configured for displaying a signal, a computer configured for displaying the weight and/or a signal (e.g., out of product signal), or an audible alarm can be activated to provide a alert when the product weight reaches predetermined weight. Other additional low or out of product signals could also be used and an individual skilled in the art would reasonably understand their direct application. In alternate embodiments, one or more of the holder magnetic elements and/or the stationary magnetic elements may be replaced by one or more of a reed switch, a Hall-effect sensor, a proximity sensor, an infrared switch, and an optical switch for providing an indication (e.g., by triggering the indicator) when the product weight is at or below a predetermined weight. In such embodiments, the movement of the container holder may be induced by mechanical elements (e.g., springs) rather than magnetic elements.

In certain embodiments, the circuit can be configured such that it may either be open or closed based on proximity to the container holder, contact with a switch or based on whether an optical beam is intercepted by the container holder. For instance, the circuit may be in a "normally open" position, where the circuit is initially open. The circuit may close when the holder magnetic elements are in close proximity to the circuit, when a contact point in the circuit is contacted by the container holder, or when the optical beam is intercepted by the container holder. Closing the circuit may trigger an indicator. In such embodiments, the contact, proximity or optical switches may be placed proximate the axial location of the container holder corresponding to a nearly empty container, or when the weight of the product has reached one or more predetermined levels. Alternatively, the circuit may be in a "normally closed" position, wherein the circuit may be initially closed, and the circuit may open when the magnetic elements are away from the circuit, when a contact point in the circuit is no longer contacted by the container holder, or when the optical beam is not intercepted by the container holder. Closing the circuit may trigger an indicator. In such embodiments, an indicator which is normally indicating (e.g., a LED showing green light) is switched off and/or a second circuit is triggered to indicate that the product weight is below pre-determined weights. In such embodiments, the contact switch, the proximity switch or the optical switch may be positioned proximate the axial location of the container holder corresponding to a maximum product weight.

Figure 14:
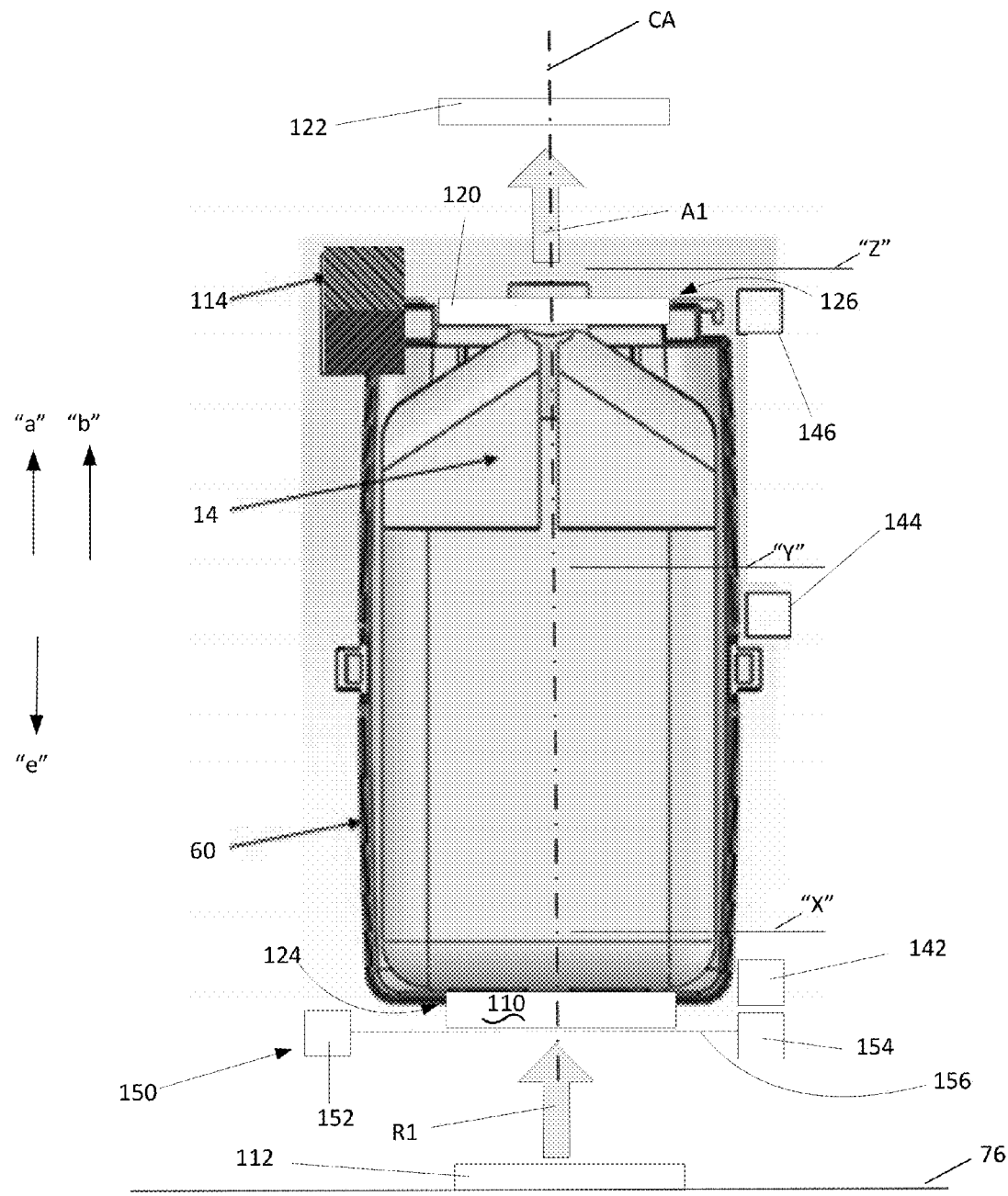
FIG. 14 is a schematic of a magnetic system coupled to a container holder of a dispenser according to some embodiments.

In a non-limiting exemplary embodiment best seen in FIG. 14, the dispenser 10 includes a reed switch 142. The particulars of the reed switch 142 do not limit the scope of the invention, and any reed switch known in the art may be provided. Initially, when the container 14 is full, the holder magnetic elements (e.g., first holder magnetic element 110) may be distal to the reed switch 142. As the dispenser 10 dispenses the product 12, the container holder 60 moves vertically upwards bringing the holder magnetic elements (e.g., first holder magnetic element 110) proximal to reed switch 142. When a holder magnetic element (e.g., first holder magnetic element 110 or second holder magnetic element 120) is proximal to the reed switch 142 the reed switch 142 may be triggered, and an indication may be provided (e.g., via indicator 114 coupled to the reed switch 142). The indication may be correlated with the position of the container holder 60 along the container holder axis 'CA' and/or the weight of the product 12 remaining in the container 14. FIG. 14 shows three possible axial positions 'X', 'Y' and 'Z' where the reed switch 142 may be positioned, but any number of axial positions of the reed switch 142 can be easily contemplated. Alternatively, a plurality of reed switches 142, 144, and 146 may be positioned at several locations along the container holder axis 'CA'. As a holder magnetic element (e.g., first holder magnetic element 110) is proximal to a reed switch 142, the reed switch 142 may trigger the indicator 114. In such embodiments, each of the reed switches 142, 144 and 146 may correspond to an axial position of the container holder 60 and/or a predetermined weight of the product 12 remaining in the container holder 60. For instance, the dispenser 10 may include a first reed switch 142 which can be triggered when a weight of approximately 300 grams is remaining in the container 14, a second reed switch 144 that can be triggered when a weight of approximately 150 grams is remaining in the container 14, and a third reed switch 146 that can be triggered when the container 14 is approximately empty.

In the embodiment illustrated in FIG. 14, a contact switch (not shown) may be used instead of or in addition to one or more holder magnetic elements (e.g., first and second holder magnetic elements 110, 120) and first and second stationary magnetic elements 112, 122 and/or one or more reed switches 142, 144 and 146. The contact switch may be closed by the container holder 60 when the container holder 60 moves along the container holder axis 'CA' from a first position (e.g., corresponding to when the container 14 is full), to a second position (e.g., corresponding to when the product weight is at or below a first pre-determined weight vertically above the first position along the container holder axis 'CA'). When the contact switch is closed, an indication (e.g., via a LED lamp, a signal read out by a display etc.) may be triggered to provide information regarding the product weight to a user.

In the embodiment illustrated in FIG. 14, a proximity sensor (not shown) may be used instead of or in addition to one or more reed switches 142. The proximity sensor can be triggered if the container holder 60 is distal to the proximity sensor. Thus, the proximity sensor can be positioned proximal to the container holder 60 (e.g., near axial faces 124, 126 of the container holder 60) when the container 14 is nearly full. As the container holder 60 moves upward, the container holder 60 moves away from the proximity sensor, thus triggering the proximity sensor to provide an indication (e.g., via a LED lamp, a signal read out by a display etc.) to the user. The proximity sensor can be configured such that it is triggered when the weight of the product remaining in the container 14 is at or below a first pre-determined weight. Alternatively, the proximity sensor can be configured such that it is triggered when the container holder 60 reaches discrete axial positions along the container holder axis 'CA'.

In certain embodiments, the dispenser may include a load cell (not shown). The load cell may be configured for producing an electrical signal based on a force. The load cell can include one or more strain gauges. The load cell may be configured to produce an electrical signal that may be coupled to the indicator of the dispenser. Alternatively, the electrical signal generated by the load cell can be coupled to a computer, and may be calibrated with the weight of the product remaining in the container. Thus, the weight of the product can be directly read by a user, without regard to the position of the container holder. Alternatively, both the position of the container holder and the weight of the product may be read by the computer via the load cell and one or more proximity sensors, reed switches, etc. In an exemplary embodiment, the load cell may be directly coupled to the container instead of magnetic elements. Such embodiments allow directly inferring the weight of the product in the container, without using stationary or holder magnetic elements. In such embodiments, the load cell can include a transducer that converts weight of the product into an electric signal that may be displayed, coupled to an indicator, or transferred to a computer. In other embodiments, the load cell may be provided in addition to the holder and stationary magnetic elements. In such embodiments, the load cell can include a transducer that converts the force response of the stationary and/or holder magnetic elements into an electrical signal that can be displayed, coupled to an indicator, or transferred to a computer The dispenser 10 may include an infrared or an optical switch 150 as seen in FIG. 14. The optical or infrared switch 150 may be triggered may include an optical emitter 152 adapted to emit a beam 156 (e.g., a laser beam) and an optical detector 154 in line with the optical emitter 152. As shown in FIG. 13, the optical switch 150 may be positioned near an axial face 126 of the container holder 60. Initially, the container holder 60 may intercept the beam 156 from the optical emitter 152 and the optical detector 154 may not receive the beam 156. When the container holder 60 moves vertically upwards, the optical detector 154 may receive the beam 156 emitted by the emitter 152, thus closing the "circuit" to produce an indication (e.g., via indicator 114 or a LED lamp, a signal which could be read out by a display etc.). The indication may correspond to the position of the container holder 60 along the container holder axis 'CA' and/or the weight of the product remaining in the container 14. Alternatively, the optical switch 150 may be positioned above the axial face 126 of the container holder 60 (not illustrated). Initially, when the container 14 is full, the beam 156 emitted by an optical emitter 152 is received by the optical detector 154. However, as the weight of the product 12 in the container 14 decreases, the container holder 60 moves upwards and intercepts the beam 156 emitted by the optical emitter 152. As the container holder 60 intercepts the beam, the "circuit" is interrupted, and an indicator coupled to the optical switch 150 may be triggered alerting the user that the weight of the product 12 in the container 14 is at or below a predetermined weight.

Referring back to FIGS. 3 and 4, in some embodiments of the invention, in addition to an indicator 114, a sign 116 may be coupled to the container holder 60. As best seen in FIGS. 3 and 4, the sign 116 can move vertically in conjunction with the container holder 60. The sign 116 may include markings, patterns, or other indicia that represent a level or levels of product 12 remaining within the container 14. The sign 116 may include numerals corresponding to predetermined weight thresholds. For instance, the sign 116 may include a first predetermined weight (e.g., 300 grams) printed therein to indicate to a user that the weight of the product 12 is at or below the first predetermined weight. The sign 116 may have a second predetermined weight (e.g., 150 grams) printed therein. The sign 116 may include the word "EMPTY" or "REPLACE" printed therein. The positioning of the numerals or other indicia may be correlated with the movement of the container holder 60, such that when the product 12 reaches a first predetermined weight (e.g., 300 grams), the magnetic forces may move the container 14 such that the sign 116 displays the numerals "300" to the user. As the dispenser 10 continues to dispense, the magnetic forces may continue to move the container 14. When the product 12 reaches the second predetermined weight (e.g., 150 grams) such that the sign 116 displays the numerals "150" to the user. Further, the sign 116 may display the words "EMPTY" or "REPLACE" when the weight of the product 12 is substantially low in comparison to its initial weight (e.g., 10 grams out of 3000 grams left). Alternatively, the sign 116 may be configured to display the words "EMPTY" or "REPLACE" when the container 14 is substantially empty. The sign 116 may be connected to a wall of the container holder 60 by threaded fasteners (not shown) within slots (not shown) formed in the container holder 60. Additionally, some vertical adjustment of the sign 116 may be permitted to allow calibrating or fine tuning the location of the sign 116 relative to the container holder 60. Although not shown, the sign 116 may be in alignment with the indicator window 130 of the door 36, when the container holder 60 is in place within the housing 20 (e.g., held by recessed tracks) and the door 36 is closed.

As described herein, embodiments of the invention provide an indication to a user or an operator, alerting the user or operator when a level or weight of a product in the container has reached certain predetermined levels/weights. The predetermined levels or weights may correspond to the minimum level or weight necessary to perform a task (e.g., disinfecting a facility). Embodiments of the invention can include one or more magnetic elements which can be configured for providing a user with any number of indications corresponding to a certain level or weight of the product remaining in the container. Thus, a user may plan for replacing and/or restocking the supply of product upon receiving an indication. Such embodiments may facilitate maintain a smaller inventory as the user/operator can restock when needed rather than storing a large inventory of products. This may lead to reduced lead times and lower cost due to a smaller inventory maintained in a facility. Knowledge of weight or level of the product remaining in the container also facilitates better compliance with chemical safety regulations, as the user may determine whether the chemical product in the container may be safely disposed and/or recycled.

Thus, embodiments of the invention are disclosed. Although the present invention has been described in considerable detail with reference to certain disclosed embodiments, the disclosed embodiments are presented for purposes of illustration and not limitation and other embodiments of the invention are possible. One skilled in the art will appreciate that various changes, adaptations, and modifications may be made without departing from the spirit of the invention.

What is claimed is:

1. A dispenser for dispensing a product, comprising:
a housing;
a container supported by the housing, the container adapted to store the product;
a container holder supporting the container, the container holder adapted to move vertically along a container holder axis within the housing; and
a first holder magnetic element positioned on the container holder;
a first stationary magnetic element positioned external to the container holder,
the first holder magnetic element and the first stationary magnetic element interacting to create a first magnetic force therebetween,
the first magnetic force inducing the container holder to move along the container holder axis in a first direction, wherein the position of the container holder along the container holder axis is correlated with a weight of the product remaining in the container.

2. The dispenser of claim 1 further comprising, a second holder magnetic element positioned on the container holder and a second stationary magnetic element positioned external to the container holder, the second holder magnetic element adapted to interact with the second stationary magnetic element to effect a second magnetic force therebetween, the second magnetic force inducing the container holder to move along the container holder axis in a second direction.

3. The dispenser of claim 2, wherein the first and second directions are parallel to a vertically upward direction.

4. The dispenser of claim 2, wherein the second stationary magnetic element is a ferromagnetic material.

5. The dispenser of claim 2, wherein the first stationary magnetic element is positioned axially opposite to the second stationary magnetic element.

6. The dispenser of claim 2, wherein the first holder magnetic element is positioned on a first face of the container holder, the first face intersecting the container holder axis, and the second holder magnetic element is positioned on a second face of the container holder, the second face intersecting the container holder axis and being axially opposite to the first face.

7. The dispenser of claim 2, wherein the first magnetic force is a repellant force adapted to move the first holder magnetic element away from the first stationary magnetic element.

8. The dispenser of claim 2, wherein the second magnetic force is an attraction force adapted to move the second holder magnetic element towards the second stationary magnetic element.

9. The dispenser of claim 2, wherein the first magnetic force is linearly proportional to a distance between the first holder magnetic element and the first stationary magnetic element.

10. The dispenser of claim 2, wherein the first magnetic force varies non-linearly with a distance between the first holder magnetic element and the first stationary magnetic element.

11. The dispenser of claim 1 further comprising an indicator, the indicator adapted to provide an indication to a user when the weight of the product in the container is below a first pre-determined weight of the product.

12. The dispenser of claim 11 wherein the first magnetic force is adapted to initiate movement of the container holder when the weight of the product in the container is less than the first pre-determined weight of the product, the movement of the container holder actuating the indicator to provide a first indication to the user.

13. The dispenser of claim 12 wherein the indicator provides a second indication to the user when the weight of the product in the container is less than a second pre-determined weight of the product.

14. The dispenser of claim 12, wherein the container holder reaches a second position along the container holder axis when the container is substantially empty.

15. The dispenser of claim 12, further comprising a sensor triggered by the movement of the container holder, the sensor providing indication of the weight of the product remaining in the container based on an axial position of the container holder along the container holder axis, wherein the sensor includes one or more of a reed switch, a proximity sensor, a load cell, contact switch, an infrared switch, and an optical switch.

16. The dispenser of claim 1, wherein the first holder magnetic element includes a plurality of magnets positioned on a periphery of the container holder.

17. The dispenser of claim 16, wherein the plurality of magnets is positioned on a first face of the container holder, the first face intersecting the container holder axis, the first face being rectangular in shape, wherein each of the plurality of magnets are positioned adjacent a vertex of the first face.

18. The dispenser of claim 1, wherein the first holder magnetic element is an annular magnet positioned on a first face of the container holder, the first face intersecting with the container holder axis at a center of the first face, such that a center of the annular magnet substantially coincides with the center of the first face of the container holder.

19. The dispenser of claim 1, wherein the first holder magnetic element and the first stationary magnetic element are each independently configurable to have a force response, such that the first magnetic force is of a predetermined magnitude when the first holder magnetic element is at a predetermined distance from the first stationary magnetic element.

20. The dispenser of claim 1, wherein the first holder magnetic element and the first stationary magnetic element are each independently configurable to have a force response, such that the first magnetic force is of a predetermined magnitude when the weight of the product in the container is at a predetermined weight.

21. The dispenser of claim 1, further comprising at least one of a first magnetic latch, a first mechanical latch, and a first electrical latch, the first magnetic latch, the first mechanical latch or the first electrical latch configured for exerting a first latching force to hold the container holder at a first axial location, the first magnetic latch, the first mechanical latch or the first electrical latch adapted to release the container holder from the first axial location when the first magnetic force exceeds the first latching force.

22. The dispenser of claim 21, further comprising at least one of a second magnetic latch, a second mechanical latch, and a second electrical latch, the second magnetic latch, the second mechanical latch or the second electrical latch configured for exerting a second latching force to hold the container holder at a second axial location, the second magnetic latch, the second mechanical latch or the second electrical latch adapted to release the container holder from the second axial location when the first magnetic force exceeds the second latching force.

23. The dispenser of claim 1, wherein the first magnetic force induces the container holder to move along the container holder axis when the first magnetic force is greater than the weight of the product in the container.

24. A dispenser for dispensing a product, comprising:
a housing;
a container supported by the housing, the container adapted to store the product;
a first holder magnetic element positioned on the container; and
a first stationary magnetic element positioned external to the container,
the first holder magnetic element and the first stationary magnetic element interacting to create a first magnetic force therebetween,
the first magnetic force inducing the container to move along a container axis in a first direction, wherein the position of the container along the container axis is correlated with a weight of the product remaining in the container.

25. The dispenser of claim 24 further comprising, a second holder magnetic element positioned on the container and a second stationary magnetic element positioned external to the container, the second holder magnetic element adapted to interact with the second stationary magnetic element to effect a second magnetic force therebetween, the second magnetic force inducing the container to move along the container axis in a second direction.

26. The dispenser of claim 24 further comprising, a sensor triggered by the movement of the container, the sensor providing indication of the weight of the product remaining in the container based on an axial position of the container along the container axis.

* * * * *